(12) United States Patent
Lee et al.

(10) Patent No.: US 9,175,330 B2
(45) Date of Patent: Nov. 3, 2015

(54) METHOD FOR SCREENING AND QUANTIFYING ISOPRENE BIOSYNTHESIS ENZYME ACTIVITY

(71) Applicant: Korea Research Institute of Bioscience and Biotechnology, Daejeon (KR)

(72) Inventors: Seung-Goo Lee, Yuseong-gu (KR); Seo Hyeon Kim, Daejeon (KR); Jongsik Gam, Daejeon (KR); Eugene Rha, Daejeon (KR); Haseong Kim, Daejeon (KR); Su-Lim Choi, Daejeon (KR); EuiSung Choi, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 13/771,952

(22) Filed: Feb. 20, 2013

(65) Prior Publication Data
US 2014/0235502 A1 Aug. 21, 2014

(51) Int. Cl.
*C12Q 1/02* (2006.01)
*C12Q 1/25* (2006.01)
*C40B 30/08* (2006.01)
(Continued)

(52) U.S. Cl.
CPC .. *C12Q 1/25* (2013.01); *C12Q 1/68* (2013.01); *C12Q 1/6897* (2013.01); *C12N 15/1086* (2013.01); *C12Q 1/02* (2013.01); *C40B 30/08* (2013.01)

(58) Field of Classification Search
None
See application file for complete search history.

(56) References Cited

U.S. PATENT DOCUMENTS

2010/0003716 A1* 1/2010 Cervin et al. ............ 435/40.5
2012/0238470 A1* 9/2012 Lee et al. ............... 506/11

FOREIGN PATENT DOCUMENTS

WO WO 2010143871 A2 * 12/2010

OTHER PUBLICATIONS

Casavant et al., "Use of a site-specific recombination-based biosensor for detecting bioavailable toluene and related compounds on roots," Environ. Microbiol. 2003, 5:238-249.*

(Continued)

*Primary Examiner* — Samuel Woolwine
*Assistant Examiner* — Kaijiang Zhang
(74) *Attorney, Agent, or Firm* — Hultquist, PLLC; Steven J. Hultquist; Mary B. Grant

(57) ABSTRACT

A method of performing high-throughput screening of various enzymatic activities with high sensitivity using artificial genetic circuits is provided. Particularly, the invention is screening and quantifying the activity of isoprene biosynthesis enzymes using an artificial genetic circuit capable of sensing isoprene. The artificial genetic circuit comprises an isoprene-sensing transcriptional regulator which recognizes isoprene, at least one reporter gene, a isoprene-sensing transcriptional regulator binding region and promoters for genes encoding isoprene-sensing transcriptional regulators and reporter proteins.

The artificial genetic circuit detects isoprene liberated from many enzymatic reactions and measures the activity of reporter genes. This system is widely applicable for high throughput and quantitative screening of isoprene biosynthesis enzymes and MEP/MVA pathway enzymes.

Therefore, the invention can be advantageously used in the protein engineering technology for enzyme modification. Particularly, it can provide a quantitative investigation of enzymatic activity, and thus can be applied to molecular evolution technology.

13 Claims, 11 Drawing Sheets

(51) Int. Cl.
*C12Q 1/68* (2006.01)
*C12N 15/10* (2006.01)

(56) References Cited

OTHER PUBLICATIONS

Byrne, A., et al., "Cascade regulation of the toluene-3-monooxygenase operon (tbuA1UBVA2C) of *Burkholderia pickettii* PKO1: role of the tbuA1 promoter (PtbuA1) in the expression of its cognate activator, TbuT", "Journal of Bacteriology", Nov. 1996, pp. 6327-6337, vol. 178, No. 21.

Pavel, H., et al., "An aromatic effector specificity mutant of the transcriptional regulator DmpR overcomes the growth constraints of *Pseudomonas* sp. strain CF600 on para-substituted methylphenols", "Journal of Bacteriology", Dec. 1994, pp. 7550-7557, vol. 176, No. 24.

Ramos, J., et al., "Transcriptional Control of the *Pseudomonas* TOL Plasmid Catabolic Operons Is Achieved Through an Interplay of Host Factors and Plasmid-Encoded Regulators", "Annu. Rev. Microbiol.", Oct. 1997, pp. 341-373, vol. 51.

Yang, J., et al., "Enhancing production of bio-isoprene using hybrid MVA pathway and isoprene synthase in *E. coli* ", "PLoS One", Apr. 27, 2012, pp. e33509 1-e33509 7, vol. 7, No. 4.

* cited by examiner

FIG. 7

```
IspSm1 : MACSVSTENVSFTETETETRRSANYEPNSWDYDYLSSDTDESIEVYKDKAKKLEAEVRREINNEKAEFLTLLELIDNVQRLGLGYRFESDIRRALDRFV : 100
IspSm2 : MACSVSTENVSFTETETETRRSANYEPNSWDYDYRLSSDTDESIEVYKDKAKKLEAEVRREINNEKAEFLTLLELIDNVQRLGLGYRFESDIRRALDRFV : 100
         MACSVSTENVSFTETETETRRSANYEPNSWDYDY  LSSDTDESIEVYKDKAKKLEAEVRREINNEKAEFLTLLELIDNVQRLGLGYRFESDIRRALDRFV

IspSm1 : SSGGFDAVTKTSLHATALSFRLLRQHGFEVSQEAFSGFKDQNGNFLENLKEDIKAILSLYEASFIALEGENILDEAKVFAISHLKELSEEKIGKDLAEQV : 200
IspSm2 : SSGGFDAVTKTSLHATALSFRLLRQHGFEVSQEAFSGFKDQNGNFLENLKEDIKAILSLYEASFIALEGENILDEAKVFAISHLKELSEEKIGKDLAEQV : 200
         SSGGFDAVTKTSLHATALSFRLLRQHGFEVSQEAFSGFKDQNGNFLENLKEDIKAILSLYEASFIALEGENILDEAKVFAISHLKELSEEKIGKDLAEQV

IspSm1 : NHALELPIHRRTQRLEAVLSIEAYRKKEDADQVLLELAILDYNMIQSVYQRDLRETSRWWRRVGIATKLHFARDRLIESFYWAVGVAFEPQYSDCRNSVA : 300
IspSm2 : NHALELPIHRRTQRLEAVLSIEAYRKKEDADQVLLELAILDYNMIQSVYQRDLRETSRWWRRVGIATKLHFARDRLIESFYWAVGVAFEPQYSDCRNSVA : 300
         NHALELPIHRRTQRLEAVLSIEAYRKKEDADQVLLELAILDYNMIQSVYQRDLRETSRWWRRVGIATKLHFARDRLIESFYWAVGVAFEPQYSDCRNSVA

IspSm1 : KMFSFVTIIDDIYDVYGTLDELELFTNAVERWDVNAIDDLPDYMKLCFLALYNTINEIAYDNLKEKGENILPYLTKAWADLCNAFLQEAKWLYNKSTPTF : 400
IspSm2 : KMFSFVTIIDDIYDVYGTLDELELFTNAVERWDVNAIDDLPDYMKLCFLALYNTINEIAYDNLKEKGENILPYLTKAWADLCNAFLQEAKWLYNKSTPTF : 400
         KMFSFVTIIDDIYDVYGTLDELELFTNAVERWDVNAIDDLPDYMKLCFLALYNTINEIAYDNLKEKGENILPYLTKAWADLCNAFLQEAKWLYNKSTPTF

IspSm1 : DDYFGNAWKSSSGPLQLVFAYFAVVQNIKKEEIENLQKYHDIISRPSHIFRLCNDIASASAEIARGETANSVSCYMRTKGISEELATESVMNLIDETWKK : 500
IspSm2 : DDYFGNAWKSSSGPLQLVFAYFAVVQNIKKEEIENLQKYHDIISRPSHIFRLCNDIASASAEIARGETANSVSCYMRTKGISEELATESVMNLIDETWKK : 500
         DDYFGNAWKSSSGPLQLVFAYFAVVQNIKKEEIENLQKYHDIISRPSHIFRLCNDIASASAEIARGETANSVSCYMRTKGISEELATESVMNLIDETWKK

IspSm1 : MNKEKLGGSLFAKPFVETAINLARQSHCTYHNGDAHTSPDELTRKRVLSVITEPILPFER- : 560  (SEQ ID NO: 10)
IspSm2 : MNKEKLGGSLFAKPFVETAINLARQSHCTYHNGDAHTSPDELTRKRVLSVITEPILPFER- : 560  (SEQ ID NO: 8)
         MNKEKLGGSLFAKPFVETAINLARQSHCTYHNGDAHTSPDELTRKRVLSVITEPILPFER
```

US 9,175,330 B2

METHOD FOR SCREENING AND QUANTIFYING ISOPRENE BIOSYNTHESIS ENZYME ACTIVITY

FIELD OF THE INVENTION

The present invention relates to a novel genetic method of detecting and quantifying target enzyme activity. More specifically, the invention relates to a novel method of screening (detecting) isoprene biosynthesis enzyme activity using an artificial genetic circuit capable of sensing isoprene. The method can be applied for the improvement of isoprene biosynthesis enzymes and pathways in bacterial system.

DESCRIPTION OF RELATED ART

Biocatalysts are recognized as one of the key components for "sustainable chemistry development," such as the biological syntheses of biopolymers, bioenergy, industrial chemicals etc, and various efforts have been made to obtain better enzymes having new chemical reactivity, specificity, and stability. However, mining of DNA sequence databases has problems like limited information on new catalytic activities and screenings using classical methods such as instrumental analysis of enzyme products have suffered from low throughput and high cost of assay methods. In addition, although some industrial enzymes (e.g., amylase, lipase, protease, etc.) have been screened by the examination of cell growth or halo formation on solid media, the correlation between the phenotype and the enzyme activity are hardly quantitative.

Thus, there have been demands for the development of high-throughput and quantitative methods to detect the activities of industrially important enzymes. A quantitative screening technology will help to identify new biocatalysts from microbial genomes or metagenomes that have emerged as important resources in modern biotechnology. Furthermore, the technology can be applied to enable the effective engagement of directed evolution technology to acquire chemical reactivity, specificity, and stability of enzymes from existing genes.

Among enzymes in biosynthesis pathways, isoprene synthase (IspS) catalyzes a key step that can produce isoprene which is used as a raw material for automobile tires and medical supplies. To date, the quantification of isoprene produced by the activity of IspS has relied mainly on the use of gas chromatography (GC). In the method, isoprene synthesized in complicated fermentation facilities such as large-scale bioreactors was monitored after the emission gas was captured from the headspace of fermentation equipment. Therefore, the GC analysis is not an effective method for the rapid screening or directed evolution that requires handling large sizes of genetic libraries. The sampling and GC analyses of isoprene gas are too time consuming, costly, and laborious to be used in search for new enzymes from a large size library. Thus, there is a large demand for a method that can measure the activities of enzymes in a simpler, more rapid and cost-effective manner.

The present invention provides such a method.

The above information disclosed in this Background section is only for enhancement of understanding of the background of the invention and therefore it may contain information that does not form the prior art that is already known in this country to a person of ordinary skill in the art.

SUMMARY OF THE INVENTION

It is an object of the present invention to provide a method of detecting and screening isoprene biosynthesis enzyme activity using an artificial genetic circuit which recognizes isoprene.

Another object of the present invention is to provide a method of quantifying isoprene biosynthesis enzyme activity using an artificial genetic circuit which recognizes isoprene.

To achieve the above objects, the present invention provides a method of detecting or screening the activity of one or more isoprene biosynthesis enzymes using an artificial genetic circuit, the method comprising the steps of:
(a) providing an artificial genetic circuit for detecting isoprene, the artificial genetic circuit comprising (i) a gene encoding an isoprene-sensing transcriptional regulator which recognizes isoprene, (ii) at least one reporter gene selected from the group consisting of fluorescence protein-encoding genes and antibiotic resistance genes, and (iii) a gene expression regulatory region consisting of a promoter regulating the expression of the isoprene-sensing transcriptional regulator, a region to which the isoprene-sensing transcriptional regulator binds to induce the expression of a downstream reporter gene, and a promoter regulating the expression of the reporter gene;
(b) providing a clone or gene library containing one or more of a gene encoding an isoprene biosynthesis enzyme;
(c) introducing the clone or gene library and the artificial gene circuit for detecting isoprene into host microorganisms to prepare recombinant microorganisms;
(d) treating the recombinant microorganisms with a compound capable of liberating isoprene by an enzymatic reaction; and
(e) detecting the activity of the reporter protein whose expression is induced by sensing isoprene liberated by the enzymatic reaction.

The present invention also provides a method of detecting or screening the activity of one or more isoprene biosynthesis enzymes using an artificial genetic circuit, the method comprising the steps of:
(a) providing microorganisms containing in their chromosomal DNA or cytoplasm an artificial genetic circuit for detecting isoprene, the artificial genetic circuit comprising (i) a gene encoding an isoprene-sensing transcriptional regulator which recognizes isoprene, (ii) at least one reporter gene selected from the group consisting of fluorescence protein-encoding genes and antibiotic resistance genes, and (iii) a gene expression regulatory region consisting of a promoter regulating the expression of the isoprene-sensing transcriptional regulator, a region to which the isoprene-sensing transcriptional regulator binds to induce the expression of a downstream reporter gene, and a promoter regulating the expression of the reporter gene;
(b) providing a clone or gene library containing one or more of a gene encoding an isoprene biosynthesis enzyme;
(c) introducing the clone or gene library into the microorganisms containing the artificial gene circuit for detecting isoprene to prepare recombinant microorganisms;
(d) treating the recombinant microorganisms with a compound capable of liberating isoprene by an enzymatic reaction; and
(e) detecting the activity of the reporter protein whose expression is induced by sensing isoprene liberated by the enzymatic reaction.

The present invention also provides a method of quantifying one or more isoprene biosynthesis enzymes activities using an artificial genetic circuit, the method comprising the steps of:
(a) providing an artificial genetic circuit for detecting isoprene, the artificial genetic circuit comprising (i) a gene encoding an isoprene-sensing transcriptional regulator which recognizes isoprene, (ii) at least one reporter gene selected from the group consisting of fluorescence protein-encoding genes and antibiotic resistance genes, and (iii) a gene expression regulatory region consisting of a promoter regulating the expression of the isoprene-sensing transcriptional regulator, a region to which the isoprene-sensing transcriptional regulator binds to induce the expression of a downstream reporter gene, and a promoter regulating the expression of the reporter gene;

(b) providing a clone or gene library containing one or more of a gene encoding an isoprene biosynthesis enzyme;

(c) introducing the clone or gene library and the artificial gene circuit for detecting isoprene into host microorganisms to prepare recombinant microorganisms;

(d) treating the recombinant microorganisms with a compound capable of liberating isoprene by an enzymatic reaction; and (e) quantifying the activity of the reporter protein whose expression is induced by sensing isoprene liberated by the enzymatic reaction.

The present invention also provides a method of quantifying one or more isoprene biosynthesis enzymes using an artificial genetic circuit, the method comprising the steps of:

(a) providing microorganisms containing in their chromosomal DNA or cytoplasm an artificial genetic circuit for detecting isoprene, the artificial genetic circuit comprising (i) a gene encoding a isoprene-sensing transcriptional regulator which recognizes isoprene, (ii) at least one reporter gene selected from the group consisting of fluorescence protein-encoding genes and antibiotic resistance genes, and (iii) a gene expression regulatory region consisting of a promoter regulating the expression of the isoprene-sensing transcriptional regulator, a region to which the isoprene-sensing transcriptional regulator binds to induce the expression of a downstream reporter gene, and a promoter regulating the expression of the reporter gene;

(b) providing a clone or gene library containing one or more of a gene encoding an isoprene biosynthesis enzyme;

(c) introducing the clone or gene library into the microorganisms containing the artificial gene circuit for detecting isoprene to prepare recombinant microorganisms;

(d) treating the recombinant microorganisms with a compound capable of liberating isoprene by an enzymatic reaction; and (e) quantifying the activity of the reporter protein whose expression is induced by sensing isoprene liberated by the enzymatic reaction.

The present invention also provides an artificial genetic circuit for detecting isoprene, the artificial genetic circuit comprising (i) a gene encoding an isoprene-sensing transcriptional regulator which recognizes isoprene, (ii) at least one reporter gene selected from the group consisting of fluorescence protein-encoding genes and antibiotic resistance genes, and (iii) a gene expression regulatory region consisting of a promoter regulating the expression of the isoprene-sensing transcriptional regulator, a region to which the isoprene-sensing transcriptional regulator binds to induce the expression of a downstream reporter gene, and a promoter regulating the expression of the reporter gene.

The present invention also provides a recombinant microorganism containing said artificial genetic circuit.

The present invention also provides a method of quantifying isoprene using said artificial genetic circuit, the method comprising the steps of:

(a) introducing the artificial gene circuit of claim 19 into host microorganisms to be measured; and (b) quantifying isoprene by measuring the activity of the reporter protein whose expression is induced by sensing isoprene.

The present invention also provides a gene encoding IspSm2 of SEQ ID NO: 8.

BRIEF DESCRIPTION OF THE DRAWINGS

FIG. 1(A) schematically shows a principle (GFP-based Enzyme Screening System for isoprene (IspGESS)) of screening isoprene biosynthesis enzyme activity using an artificial genetic circuit according to the present invention, and FIG. 1(B) schematically shows an IspGESS vector (pIspGESS) and also shows an enlarged structure of the gene expression regulatory region of the IspGESS vector.

FIG. 7 shows the amino acid sequence of the IspSm2 having increased activity contains a lysine-to-arginine mutation at position 35 from the amino acid sequence of IspSm1.

DETAILED DESCRIPTION OF THE INVENTION

Figure 1:
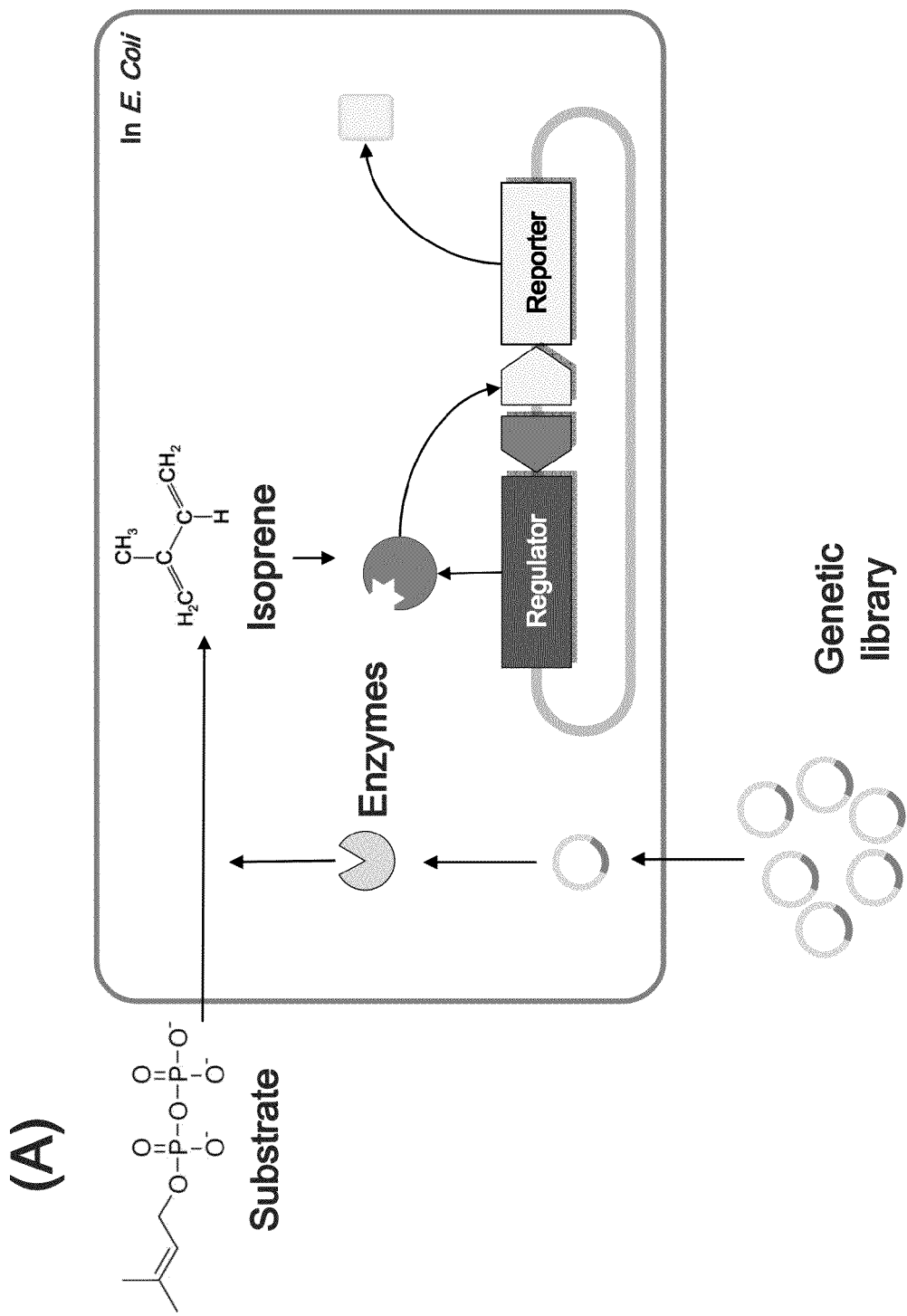
In FIG. 1, Regulator: transcriptional regulation factor; $P_T$: promoter regulating the expression of an isoprene-sensing transcriptional regulator; and $P_R$: promoter regulating the expression of a reporter.
Figure 1:
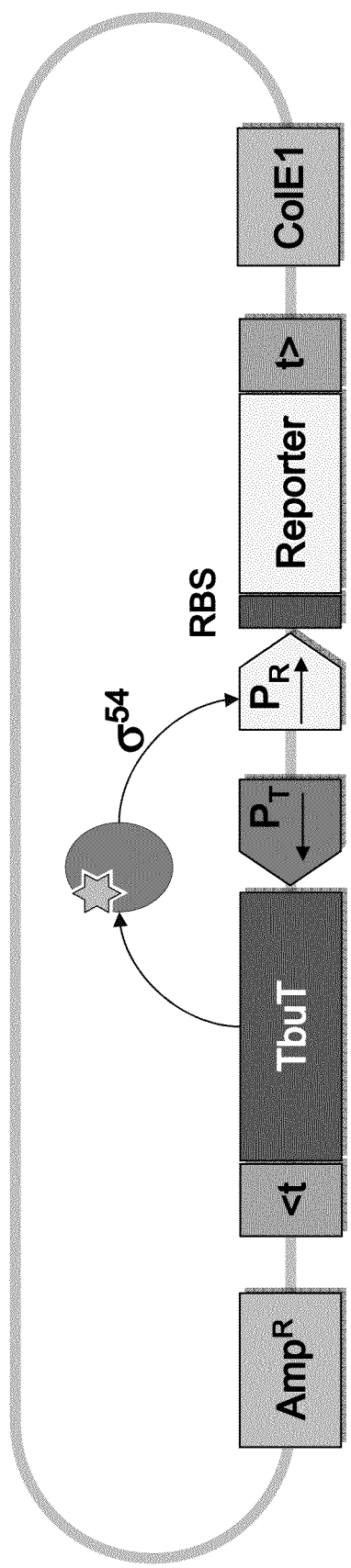

Unless defined otherwise, all technical and scientific terms used herein have the same meaning as commonly understood by one of ordinary skill in the art to which the invention pertains. Generally, the nomenclature used herein is well known and commonly employed in the art.

The present inventors have conducted studies on a high throughput and quantitative method capable of detecting isoprene compounds. In consideration of characteristics of regulatory proteins which detect isoprene in bacterial cells the inventors have designed an artificial genetic circuit recognizing isoprene biosynthetic products. As a result, the inventors found that the genetic circuit that enables quantitative measurements of the IspS activity in bacterial systems. The present inventors have confirmed that the invented technique can be efficiently and generally used for detecting improved enzyme activities from an IspS mutant library using a high-throughput flow cytometry (million/day). The present invention can be further extended to evaluate the effects of any enzymes, regulators, or metabolic pathways that affecting to the isoprene synthesis, not only the case of IspS, but also other related pathway genes.

For severe climate change and petroleum resources depletion leading to strict environmental regulation and upside price risk of oil refinery products, it is of critical concern to replace oil-based chemical feedstock with biomass-based eco-friendly materials emitting low green-house gases. Isoprene is a colorless, highly volatile compound having a melting point of −145.95° C., a boiling point of 34.067° C. and a density of 0.68 g/cm$^2$. It is obtained as a byproduct of cracking of naphtha/oil and is mainly used for the production of synthetic rubber (cis-1,4-polyisoprene) which is used as a main raw material for tires in the automobile industry. In addition, it is used as a raw material for paint, the major component of medical devices, and the like. As an alternative source of isoprene derived from petroleum, bioisoprene can be produced by means of microbial synthesis of isoprene by fermentation and collected from the gas phase of the fermentor, eliminating the need for distillation. The world market size of bioisoprene was over 1~2 billion dollars in 2007 and the market size in 2013 is predicted to be over 12 billion dollars.

Isoprene is biosynthesized from the same basic units, isopentenyl diphosphate (pyrophosphate IPP), and its isomer dimethylallyl diphosphate (DMAPP), which are synthesized from two different pathways including methylerythritol 4-phosphate (MEP) pathway and mevalonate (MVA) pathway. MVA pathway mainly exists in eukaryotes, archaebacteria, and cytosols of higher plants, while the MEP pathway is used by many eubacteria, green algae, and chloroplasts of higher plant. MVA pathway has been studied extensively for producing isoprene. The introduction of heterologous MVA pathway genes into *E. coli* has been reported to improve the productivity of carotenoids or sesquiterpenes that are synthesized from DMAPP (Yang J et al. (2012) PLoS ONE 7(4): e33509).

Isoprene synthase (EC 4.2.3.27) is an enzyme that catalyzes the chemical reaction producing isoprene and diphosphate from dimethylallyl diphosphate (DMAPP). Isoprene is highly volatile, and thus is very difficult to analyze quantitatively, and gas chromatography analysis which is generally performed requires a significant amount of isoprene.

TbuT is one of the NtrC family of transcriptional activators that regulates toluene-3-monooxygenase operon (tbuA1UBVA2C).

A NtrC family regulator consists of a combination of a domain (domain A) recognizing aromatic compounds such as toluene or phenol, a domain (domain C) having ATPase activity, and a domain (domain D) functioning to bind to DNA. Thus, when there is no aromatic compound, domain A inhibits transcription, but when an aromatic compound binds to domain A, domains C and D are activated for transcription of downstream structural genes. In recent years, a study on the use of domain A to detect new substances and a study on the modification of specificity by domain A were reported (Pavel et al., (1994) J. Bacteriol. 176(4): 7550-7557).

Typical NtrC family transcriptional activators which are known in the art include XylR, TbuT, TbmR, PcuR, MopR, TouR, PhlR and DmpR the like, and among them, the most well-known are XylR, which is involved in the metabolism of toluene and xylene in *Pseudomonas putida* (Ramos & Marques, (1997), and *Annu. Rev. Microbiol.* 51:341-372), and TbuT which is involved in the toluene degradation metabolism (Armando M. Byrne et. & RONALD H. OLSEN, (1996), and J. of Bacteriol., 6327-6337). These Ntrc family activators regulate a multifunctional operon in which a plurality of genes are expressed together, and these genes are expressed by regulation of $\sigma^{54}$-dependent transcription.

It is known that $\sigma^{54}$-dependent transcriptional regulator TbuT senses toluene and benzene, and activates expression of the tbuA1UBVA2C operon by binding to a P$_{tbuA}$ promoter. Expression of tbuT and that of the tbuA1UBVA2C operon are linked by readthrough transcription of tbuT from the toluene-3-monooxygenase promoter. Transcription of tbuT is low when the toluene-3-monooxygenase operon is uninduced and high when the expression of tbuA1UBVA2C is induced by toluene. Thus, the toluene-3-monooxygenase promoter drives the cascade expression of both the toluene-3-monooxygenase operon and tbuT, resulting in a positive feedback circuit.

It is generally known that TbuT is activated by aromatic compounds including toluene, benzene, naphthalene, catechol and chlorobenzene, but it responded slightly towards non-aromatic compounds.

The method for investigating isoprene biosynthesis enzyme activity according to the present invention requires constructing an artificial genetic circuit for sensing of isoprene released from a substrate. For this, in the present invention, GESS obtained in previous studies (U.S. Patent Application Publication No. 2012/0238470) was redesigned, thereby constructing the novel genetic circuit, IspGESS.

GESS (GFP-based enzyme screening system) is a technology of performing high-throughput screening of various enzymatic activities with high sensitivity using artificial genetic circuits. DmpR based GESS detects phenols liberated from many enzymatic reactions and allows measurement of the activity of reporter genes, such as fluorescent reporter genes and antibiotic resistance genes. This system is a widely applicable tool for high throughput and quantitative screening of diverse enzymes such as phosphatase, lipase, oxydoreductase, cellulase and so on.

Based on the GESS, a genetic circuit with a *R. pickettii*-derived TbuT expression regulator was constructed by a cloning process for replacing the dmpR of the GESS plasmid.

In one aspect, the present invention is directed to a method of detecting or screening the activity of one or more isoprene biosynthesis enzymes using an artificial genetic circuit, the method comprising the steps of: (a) providing an artificial genetic circuit for detecting isoprene, the artificial genetic circuit comprising (i) a gene encoding an isoprene-sensing transcriptional regulator which recognizes isoprene, (ii) at least one reporter gene selected from the group consisting of fluorescence protein-encoding genes and antibiotic resistance genes, and (iii) a gene expression regulatory region consisting of a promoter regulating the expression of the isoprene-sensing transcriptional regulator, a region to which the isoprene-sensing transcriptional regulator binds to induce the expression of a downstream reporter gene, and a promoter regulating the expression of the reporter gene; (b) providing a clone or gene library containing one or more of a gene encoding an isoprene biosynthesis enzyme; (c) introducing the clone or gene library and the artificial gene circuit for detecting isoprene into host microorganisms to prepare recombinant microorganisms; (d) treating the recombinant microorganisms with a compound capable of liberating isoprene by an enzymatic reaction; and (e) detecting the activity of the reporter protein whose expression is induced by sensing isoprene liberated by the enzymatic reaction.

According to the present invention, the technology (GESS: GFP-based enzyme screening system) of sensing various enzymatic activities using an artificial genetic circuit with high sensitivity in a simple manner is applied to investigate isoprene biosynthesis enzyme activity. The present invention provides a method which enables efficient investigation of isoprene biosynthesis enzyme activity from large libraries, which was not easy to investigate by conventional screening methods. The method of the present invention also has an advantage in that isoprene biosynthesis enzyme activity can be quantitatively measured.

In another aspect, the present invention also provides a method of detecting or screening the activity of one or more isoprene biosynthesis enzymes using an artificial genetic circuit, the method comprising the steps of: (a) providing microorganisms containing in their chromosomal DNA or cytoplasm an artificial genetic circuit for detecting isoprene, the artificial genetic circuit comprising (i) a gene encoding an isoprene-sensing transcriptional regulator which recognizes isoprene, (ii) at least one reporter gene selected from the group consisting of fluorescence protein-encoding genes and antibiotic resistance genes, and (iii) a gene expression regulatory region consisting of a promoter regulating the expression of the isoprene-sensing transcriptional regulator, a region to which the isoprene-sensing transcriptional regulator binds to induce the expression of a downstream reporter gene, and a promoter regulating the expression of the reporter gene; (b) providing a clone or gene library containing one or more of a gene encoding an isoprene biosynthesis enzyme; (c) introducing the clone or gene library into the microorganisms containing the artificial gene circuit for detecting isoprene to prepare recombinant microorganisms; (d) treating the recombinant microorganisms with a compound capable of liberating isoprene by an enzymatic reaction; and (e) detecting the activity of the reporter protein whose expression is induced by sensing isoprene liberated by the enzymatic reaction.

In still another aspect, the present invention also provides a method of quantifying one or more isoprene biosynthesis enzymes activities using an artificial genetic circuit, the method comprising the steps of: (a) providing an artificial genetic circuit for detecting isoprene, the artificial genetic circuit comprising (i) a gene encoding an isoprene-sensing transcriptional regulator which recognizes isoprene, (ii) at least one reporter gene selected from the group consisting of fluorescence protein-encoding genes and antibiotic resistance genes, and (iii) a gene expression regulatory region consisting of a promoter regulating the expression of the isoprene-sensing transcriptional regulator, a region to which the isoprene-sensing transcriptional regulator binds to induce the expression of a downstream reporter gene, and a promoter regulating the expression of the reporter gene; (b) providing a clone or gene library containing one or more of a gene encoding an isoprene biosynthesis enzyme; (c) introducing the clone or gene library and the artificial gene circuit for detecting isoprene into host microorganisms to prepare recombinant microorganisms; (d) treating the recombinant microorganisms with a compound capable of liberating isoprene by an enzymatic reaction; and (e) quantifying the activity of the reporter protein whose expression is induced by sensing isoprene liberated by the enzymatic reaction.

In still another aspect, the present invention also provides a method of quantifying one or more isoprene biosynthesis enzymes using an artificial genetic circuit, the method comprising the steps of: (a) providing microorganisms containing in their chromosomal DNA or cytoplasm an artificial genetic circuit for detecting isoprene, the artificial genetic circuit comprising (i) a gene encoding a isoprene-sensing transcriptional regulator which recognizes isoprene, (ii) at least one reporter gene selected from the group consisting of fluorescence protein-encoding genes and antibiotic resistance genes, and (iii) a gene expression regulatory region consisting of a promoter regulating the expression of the isoprene-sensing transcriptional regulator, a region to which the isoprene-sensing transcriptional regulator binds to induce the expression of a downstream reporter gene, and a promoter regulating the expression of the reporter gene; (b) providing a clone or gene library containing one or more of a gene encoding an isoprene biosynthesis enzyme; (c) introducing the clone or gene library into the microorganisms containing the artificial gene circuit for detecting isoprene to prepare recombinant microorganisms; (d) treating the recombinant microorganisms with a compound capable of liberating isoprene by an enzymatic reaction; and (e) quantifying the activity of the reporter protein whose expression is induced by sensing isoprene liberated by the enzymatic reaction.

In the present invention, the reporter gene and the promoter regulating the expression of the reporter gene may be operably linked to each other.

In the present invention, the region to which the isoprene-sensing transcriptional regulator binds to induce the expression of the downstream reporter gene is a region to which the isoprene-sensing transcriptional regulator binds to activate the promoter of the reporter gene such that the downstream reporter gene can be expressed. The region to which the isoprene-sensing transcriptional regulator binds to activate the promoter of the reporter gene may be OpR (operator for Reporter) region.

In the present invention, the gene encoding an isoprene-sensing transcriptional regulator, which recognizes the isoprene, and the promoter regulating the expression of the isoprene-sensing transcriptional regulator are operably linked to each other.

In the present invention, the enzymes to be investigated are isoprene biosynthesis enzymes including IspS and MEP/MVA pathway enzymes. For example, Isoprene synthase (IspS), DXP synthase (DXS), DXP reductoisomerase (DXR), CDP-ME synthase (MCT), CDP-ME kinase (CMK), ME-cPP synthase (MDS), HMBPP synthase (HDS), HMBPP reductase (HDR), IPP isomerase (IDI), geranyl diphosphate (GPP), geranylgeranyl diphosphate (GGPP), abscisic acid (ABA), atoB/phaA, mvaS, mvaA, mvaK1, mvaK2 and mvaD. In one embodiment of the present invention, the *Ralstonia pickettii*-derived toluene degradation operon (Tbu operon) regulatory protein TbuT was used.

In the present invention, the fluorescence protein may be selected from the group consisting of GFP (green fluorescent protein), EGFP (enhanced green fluorescent protein), $GFP_{UV}$ (UV-excited green fluorescent protein), RFP (red fluorescent protein), mRFP (modified red fluorescent protein), YFP (yellow fluorescent protein), mcherry, CFP (cyan fluorescent protein), mGFP (modified green fluorescent protein), ERFP (enhanced red fluorescent protein), BFP (blue fluorescent protein), EBFP (enhanced blue fluorescent protein), EYFP (enhanced yellow fluorescent protein) and ECFP (enhanced cyan fluorescent protein), and the antibiotic resistance gene may be selected from the group consisting of an ampicillin resistance gene, a kanamycin resistance gene, a chloramphenicol resistance gene and a tetracycline resistance gene.

In the present invention, the measurement of the activity of the reporter protein is performed using microcolony fluorescence image analysis, fluorescence spectrum analysis, fluorescence-activated cell sorting (FACS), or antibiotic resistance measurement.

In the present invention, the host microorganism in which the library is introduced is *E. coli, Pseudomonas*, a yeast cell, a plant cell, an animal cell or the like.

In the present invention, the artificial genetic circuit includes a gene coding for RBS (ribosome binding site), and the reporter gene can be a dual reporter gene consisting of a fluorescence protein-encoding gene and an antibiotic resistance gene.

In the present invention, the "isoprene-sensing transcriptional regulator which recognizes isoprene" can be selected from the genes of XylR, TbuT, TbmR, StyR and TodR. It will be obvious to those skilled in the art that, even when genetically mutated genes thereof are provided according to the present invention, these genetically mutated genes can show the same results. Additionally, any transcriptional regulator, which recognizes isoprene and thus can activate a promoter of a report gene, can be used.

In the present invention, as shown in FIG. 1B, the "gene expression regulatory region" is a portion regulating the artificial genetic circuit and consists of (i) a promoter regulating the expression of the isoprene-sensing transcriptional regulator that is a transcriptional regulator, (ii) a region to which the isoprene-sensing transcriptional regulator (isoprene-sensing transcriptional regulator) binds to induce the expression of a downstream reporter gene, and (iii) a promoter regulating the expression of the reporter gene. When there is no isoprene molecule, domain A of the isoprene-sensing transcriptional regulator inhibits transcription, but when a isoprene molecule binds to inhibit domain A, domains C and D show a function of activating transcription, and thus bind to the OpR (operator for reporter) region as shown in FIG. 1B, and the activity thereof is regulated by depending on $\sigma^{54}$.

As used herein, the term "promoter" means either a promoter regulating the expression of isoprene-sensing transcriptional regulator, or a promoter regulating the expression of the reporter protein. For example, the promoter is a *Ralstonia* tbuT or tbu operon promoter or a promoter for expression of general protein. For high-level expression of a foreign protein, a high-expression promoter, such as a trc, T7, lac or ara promoter can be used, and particularly, the constitutive high-expression promoter $P_{hce}$ that does not require use of an inducer. Preferably, the promoter regulating the expression of the reporter gene can be selected from the group consisting of tbuA promoter (PtbuA), tbmA promoter (PtbmA), Pu promoter. Additionally, the promoter regulating the expression of the isoprene-sensing transcriptional regulator which recognizes isoprene can be selected from the group consisting of $P_{hce}$ (hyper constitutive expression promoter), $P_{ace}$ (Acetate promoter), $P_{Trc}$ (trc promoter), $P_{T7}$ (T7 promoter), $P_{lac}$ (lac promoter) and $P_{ara}$ (arabinose promoter). It will be obvious to those skilled in the art that, even when genetically modified promoters thereof are provided according to the present invention, these genetically modified promoters can show the same results.

Specifically as shown in FIG. 1B, the promoter regulating the expression of the reporter protein is a $\sigma^{54}$-dependent promoter ($P_R$). In addition, a person skilled in the art will appreciate that the promoter is derived from *R. pickettii*, yeast or the like depending on the host of pIspGESS.

In the present invention, the artificial genetic circuit preferably comprises, in addition to the above promoter, a ribosome binding site (RBS) facilitating the expression of the reporter gene and/or a transcriptional terminator. Namely, the artificial genetic circuit comprises, in addition to the promoter, RBS and/or a transcriptional terminator, which regulates the expression of the regulatory protein.

Generally, the expression of a protein starts with the initiation codon AUG (methionine) or GUG (Valine) in mRNA, and the discrimination between the protein initiation codons AUG and GUG and the AUG or GUG residue present in the ribosome protein is determined by RBS (or Shine-Dalgarno (SD) sequence) rich in purine bases of DNA, in which RBS is known to be different between species (Stryer, L., (1995) *Biochemistry*, (4th ed.) W. H. Freeman, Chapter 34, Protein Synthesis). The artificial genetic circuit constructed in the present invention comprises a transcriptional regulator from *Pseudomonas*, which is significantly different from *E. coli*, the host of the genetic circuit. Further, for $\sigma^{54}$-dependent gene expression, a $\sigma^{54}$-binding site or a $\sigma^{54}$-dependent regulator is significantly different from that derived from *E. coli*. Thus, in order to facilitate expression of the reporter gene in the *Pseudomonas* RBS or the host *E. coli*, *E. coli* RBS or RBS that can be derived from all microbial strains can be used in the present invention. In one embodiment of the present invention, T7 RBS from bacteriophage T7 can be used.

In the present invention, the transcriptional terminator is preferably rrnBT1T2 or tL3. In addition, any transcriptional terminator that is conventionally used in the art can be used in the present invention.

In the present invention, one or more reporter genes can be selected from among fluorescence proteins and antibiotic resistance genes. In one aspect, the fluorescence protein is preferably GFP, $GFP_{UV}$ or RFP. In addition, any fluorescence protein can be used so long as it can achieve the objective of the present invention. Exemplary antibiotic resistance genes that can be used in the present invention include, but are not limited to, conventional antibiotic resistance genes, including kanamycin, chloramphenicol, and tetracycline.

In one embodiment of the present invention, the reporter gene is a dual reporter consisting of both a fluorescence protein and an antibiotic resistance gene, or a multiple reporter consisting of two or more genes. According to the present invention, the metagenomic library and the isoprene-sensing artificial genetic circuit are transformed into a suitable microbial host in a stepwise manner. The transformation is carried out using any known method. In order to increase the efficiency of the transformation, electroporation is preferably used.

In the present invention, a gene encoding the enzyme to be detected or screened is provided in the form of a clone or genetic library. For example, it can be provided in the form of a single gene, a genomic library, a metagenome or a metagenomic library, which can be applied in the molecular biological field. In addition, the single gene is provided in a form in which it is contained in a vector or a microorganism.

In still another aspect, the present invention relates to an artificial genetic circuit for detecting isoprene, and a recombinant microorganism containing the artificial genetic circuit, wherein the artificial genetic circuit comprises (i) a gene encoding an isoprene-sensing transcriptional regulator which recognizes isoprene, (ii) at least one reporter gene selected from the group consisting of fluorescence protein-encoding genes and antibiotic resistance genes, and (iii) a gene expression regulatory region consisting of a promoter regulating the expression of isoprene-sensing transcriptional regulator, a region to which the isoprene-sensing transcriptional regulator binds to induce the expression of a downstream reporter gene, and a promoter regulating the expression of the reporter.

In the present invention, the artificial genetic circuit is provided in the form of a vector or a microorganism. In the present invention, the microorganism is preferably E. coli, yeast, a plant cell or an animal cell.

According to the present invention, the microorganism transformed with the genetic circuit is cultivated to synthesize IspS and to accumulate more DMAPP or IPP in cells.

The transcriptional regulatory protein is $\sigma^{54}$-dependent and operates well in an environment in which nutrient components are limited (Sze et al., (1996) J. Bacteriol. 178: 3727-3735). For these reasons, M9 media is more suitable for high-throughput screening than LB media.

When any enzyme gene is introduced into a recombinant microorganism containing an artificial genetic circuit which senses an isoprene-, toluene- or benzene-based compound and the gene is treated with the isoprene, the concentration of the compound changes depending on the function or activity of the intracellular enzyme gene. Thus, when the quantitative increase of a reporter (such as a fluorescence reporter or an antibiotic resistance reporter), caused by the expression-inducing function of the isoprene, is investigated using various measurement techniques, including fluorescence spectrometry and antibiotic resistance measurement, intracellular and extracellular enzymatic activities can be sensed with high sensitivity. Thus, the present invention provides a novel measurement method of sensing intracellular and extracellular enzymatic activities with high sensitivity.

Moreover, a fluorescence protein or an antibiotic resistance protein, which is used as a reporter in the present invention, can be detected by a highly sensitive measurement method and remains in a specific cell without passing through the cell membrane, and individually exhibits the characteristics of a foreign gene which is expressed in the cell. Thus, because a single cell functions as an independent reactor and analyzer, several hundred to several ten million samples can be measured using fluorescence-activated cell sorting (FACS), microcolony fluorescence image analysis, fluorescence spectrum analysis, high-throughput screening with antibiotic selective medium, in order to measure the activity of a reporter whose expression was induced by sensing isoprene released by an enzymatic reaction.

In still another aspect, the present invention relates to a method of quantifying isoprene using said artificial genetic circuit, the method comprising the steps of: (a) introducing said artificial gene circuit into host microorganisms to be measured; and (b) quantifying isoprene by measuring the activity of the reporter protein whose expression is induced by sensing isoprene.

In one embodiment of the present invention, IspSm2 having isoprene synthesis activity which is two times higher than that of Populus trichocarpa-derived IspSm1 (U.S. Patent Application Publication No. 2010/0003716) was isolated by the inventive method of investigating the activity of isoprene biosynthesis enzymes using the artificial genetic circuit.

In still another aspect, the present invention relates to IspSm2, a mutant IspSm1 containing L35R (SEQ ID NO: 8).

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Construction of Artificial Genetic Circuit

The method for investigating enzymatic activity according to the present invention requires constructing an artificial genetic circuit for sensing isoprene released from a substrate. For this, the GESS genetic circuit (Korean Patent Laid-Open Publication No. 2010-0131955) obtained in previous studies was redesigned, thereby constructing the novel genetic circuit IspGESS (FIG. 1).

Figure 2:
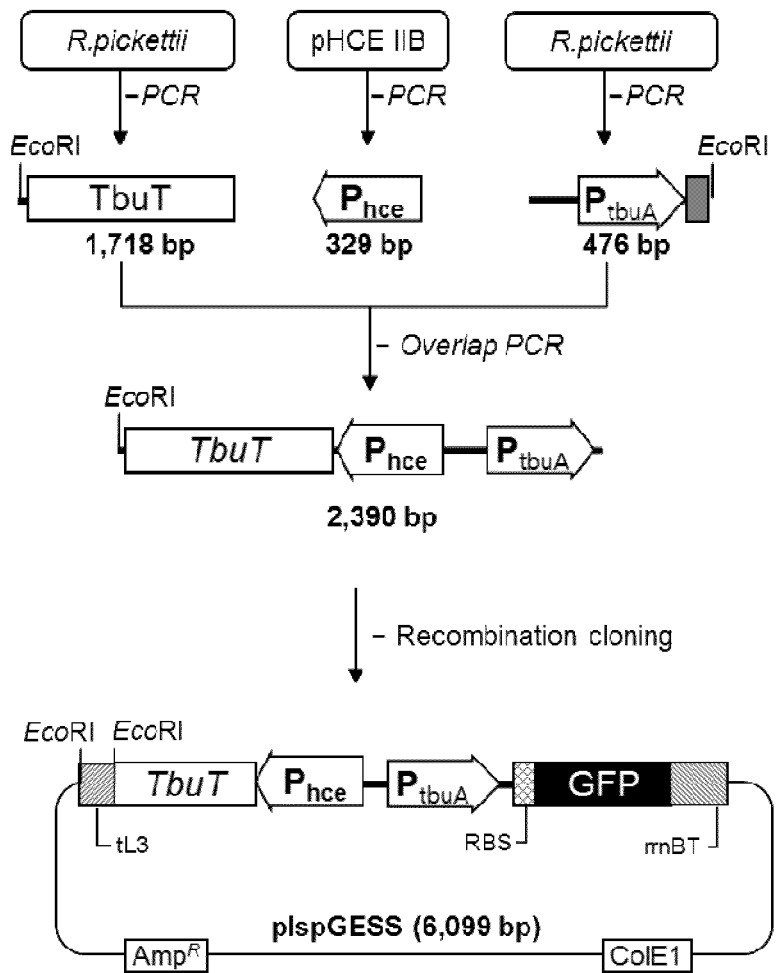
FIG. 2 shows a process of constructing pIspGESS. Specifically, PCR products of tbuT gene and $P_{tbuA}$ are derived from *R. pickettii*. PCR product of $P_{hce}$ is a highly constitutive promoter for expression of reporter protein. The three PCR products are combined by overlap PCR and cloned into the pGESS (U.S. Patent Application Publication No. 2012/0238470).

A cloning process was performed in the following manner (FIG. 2). First, a recombineering method was introduced in order to replace the regulatory gene (dmpR) and a promoter region for reporter expression with the R. pickettii-derived regulatory gene (tbuT), based on the GESS plasmid constructed in the previous study (Patent, KR1020050116672; U.S. Patent Application Publication No. 2012/0238470). A promoter for expression of TbuT ($P_{hce}$) was located at −15 bp from tbuT start codon by a restriction enzyme site and an additional sequence. The regulatory gene (tbuT) was obtained by colony PCR using a R. pickettii strain (ATCC, USA) as a template and primers of SEQ ID NOS. 1 and 2, and the $P_{tbuA}$ promoter region was also obtained by colony PCR using R. pickettii as a template and primers of SEQ ID NOS: 3 and 4. Finally, the $P_{hce}$-TbuT-$P_{tbuA}$ fragment obtained by PCR was amplified by PCR, thereby constructing IspGESS.

```
SEQ ID NO: 1 - 5'-gccattagatcttcagcttccgtcg
actgga-3'

SEQ ID NO: 2 - 5'-gatatcagctagcccttctggccg
cgataagcttgggaa-3'

SEQ ID NO: 3 - 5'-attcttaccaattgatgaa-3'

SEQ ID NO: 4 - 5'-cggggtccagttggtcgt-3'
```

Example 2

Verification of IspGESS and Analysis of Quantitative Signals for Isoprene, Toluene, Benzene and Phenol Analysis of quantitative signals of artificial genetic circuit for isoprene, toluene, benzene and phenol.

In order to examine the isoprene, toluene, benzene and phenol compounds sensing function of pIspGESS-containing recombinant E. coli, pIspGESS of Example 1 was introduced into a single colony of E. coli DH5α (NEB, USA) by heat shock, and then the E. coli colony was inoculated into an LB liquid medium (1% (w/v) trypton, 0.5% (w/v) yeast extract, and 1% (w/v) sodium chloride) supplemented with 50 μg/Ml of ampicillin and was cultured with shaking at 37° C. for 14 hours. The culture was inoculated into M9 minimal medium (containing 50 μg/Ml ampicillin, 4% glucose and 1% thiamine) at a concentration of 1% and then cultured with shaking at 37° C. for 6 hours. Various concentrations (0-2000 μM) of isoprene was added to each of the test tubes containing the culture broth, after then the culture was cultured with shaking at 30° C. for 18 hours, thereby inducing the expression of fluorescence in the culture. The intensity of intracellular fluorescence induced by each concentration of toluene was analyzed by a FACS Calibur system (Becton Dickinson, USA). As a detector, a FSC, SSC, FL1-H (excitation=488 nm, emission=530/30 nm) detector was set, and data obtained by observing 10,000 samples were analyzed using CellQuest Pro (Becton Dickinson, USA).

As a result, it was seen that the intensity of fluorescence was definitely distinguished between the presence and absence of isoprene and increased as the isoprene concentration increased. Also the fluorescence intensities increased in proportion to the increases in the concentrations of the substrates (FIG. 3(A)). It was seen that fluorescence started to be sensed from 50 μM for isoprene.

Figure 3:
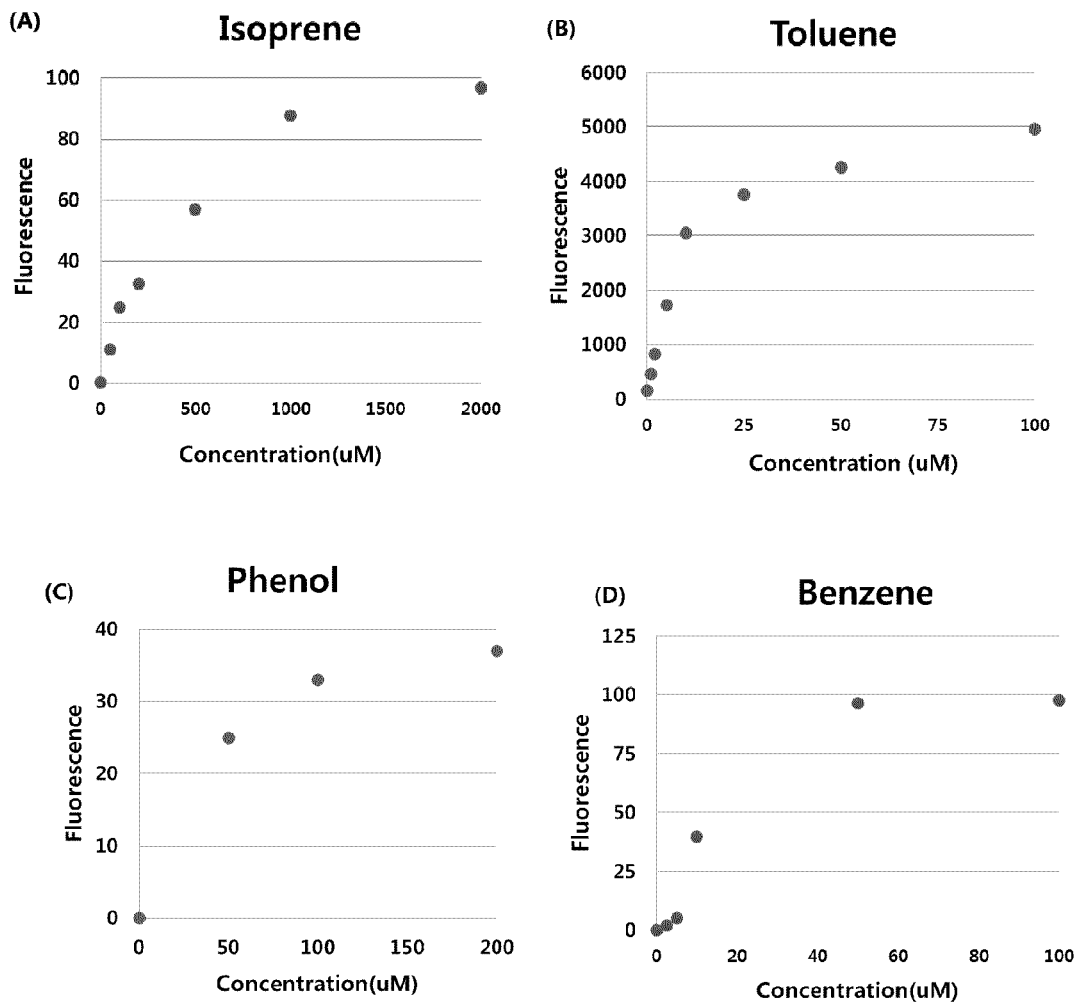
FIG. 3 shows the verification of IspGESS by measuring quantitative responses to various compounds using fluorescence-activated cell sorting (FACS). (A): the measurement of the quantitative response of IspGESS to isoprene; (B): the measurement of the quantitative response of IspGESS to toluene; (C) the measurement of the quantitative response of IspGESS to phenol; and (D) the measurement of the quantitative response of IspGESS to benzene.

Additionally, it was seen that the IspGESS responded to toluene, phenol and benzene (FIGS. 3(B), (C) and (D)). It was seen that fluorescence started to be sensed from 0.5 μM for toluene, 1 μM for benzene and 50 μM for phenol.

In conclusion, the artificial genetic circuit (IspGESS) constructed by the above-described culture senses quantitatively isoprene, toluene, phenol and benzene and is regulated by them.

Example 3

Detection of Isoprene Biosynthesis Enzyme Using IspGESS

Using the IspGESS genetic circuit according to the present invention, activity of IspSm1, *P. trichocarpa*-derived IspS (USP 2010/0003716) was sensed.

First, the IspSm1 gene was inserted into the NcoI-AvrII restriction enzyme site of a pCDF-duet vector (Novagen, USA) to prepare pCDF-IspSm1, which was then introduced into an *E. coli* BL21 (DE3) strain (NEB, USA) containing pIspGESS of Example 1 50 μg/Ml of ampicillin and 10 μg/Ml of streptomycin were added to LB liquid medium containing 0.1 mM of IPTG (isopropyl-thio-β-Dgalactopyranoside), and *E. coli* cells were cultured with shaking in the LB liquid medium at 37° C. for 16 hours. Then, the cultured cells were transferred into M9 liquid medium containing 0.1 mM IPTG and were cultured at 28° C. and 200 rpm for 20 hours. 4 ml of the culture medium was placed in a 5 ml vial into which the previously cultured bacterial strain was then inoculated at a concentration of 1%. Then, the vial was sealed with a septum and incubated. The intensity of fluorescence in the cultured cells was analyzed using a FACS Calibur system (Becton Dickinson, USA). As a detector, a FSC, SSC, FL1-H (excitation=488 nm, emission=530/30 nm) detector was set, and data obtained by observing 10,000 samples were analyzed.

Figure 4:
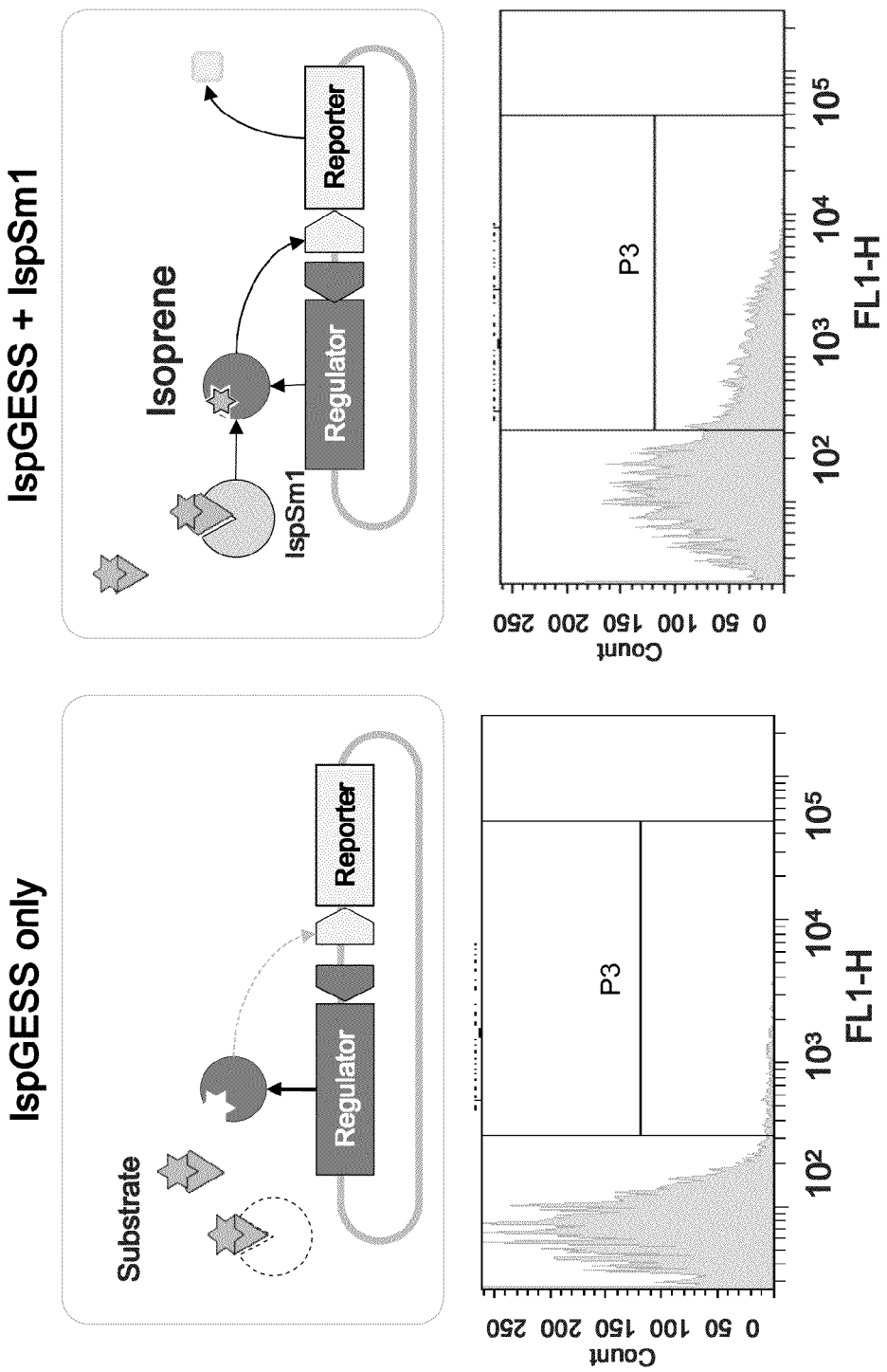
FIG. 4 shows that IspGESS can detect the isoprene synthase (IspSm1) activity using fluorescence-activated cell sorting (FACS). IspGESS with IspSm1 (FIG. 4 right) shows higher fluorescence intensity than that without IspSm1 (FIG. 4. left).

As a result, it could be observed that the intensity of fluorescence was higher in the samples containing IspSm1 than in the samples containing no IspSm1 (FIG. 4).

Based on the above results, a system for quantitative investigation of isoprene, which comprises the IspGESS genetic circuit, was constructed.

Example 4

Screening of Isoprene Synthase Using IspGESS

Figure 5:
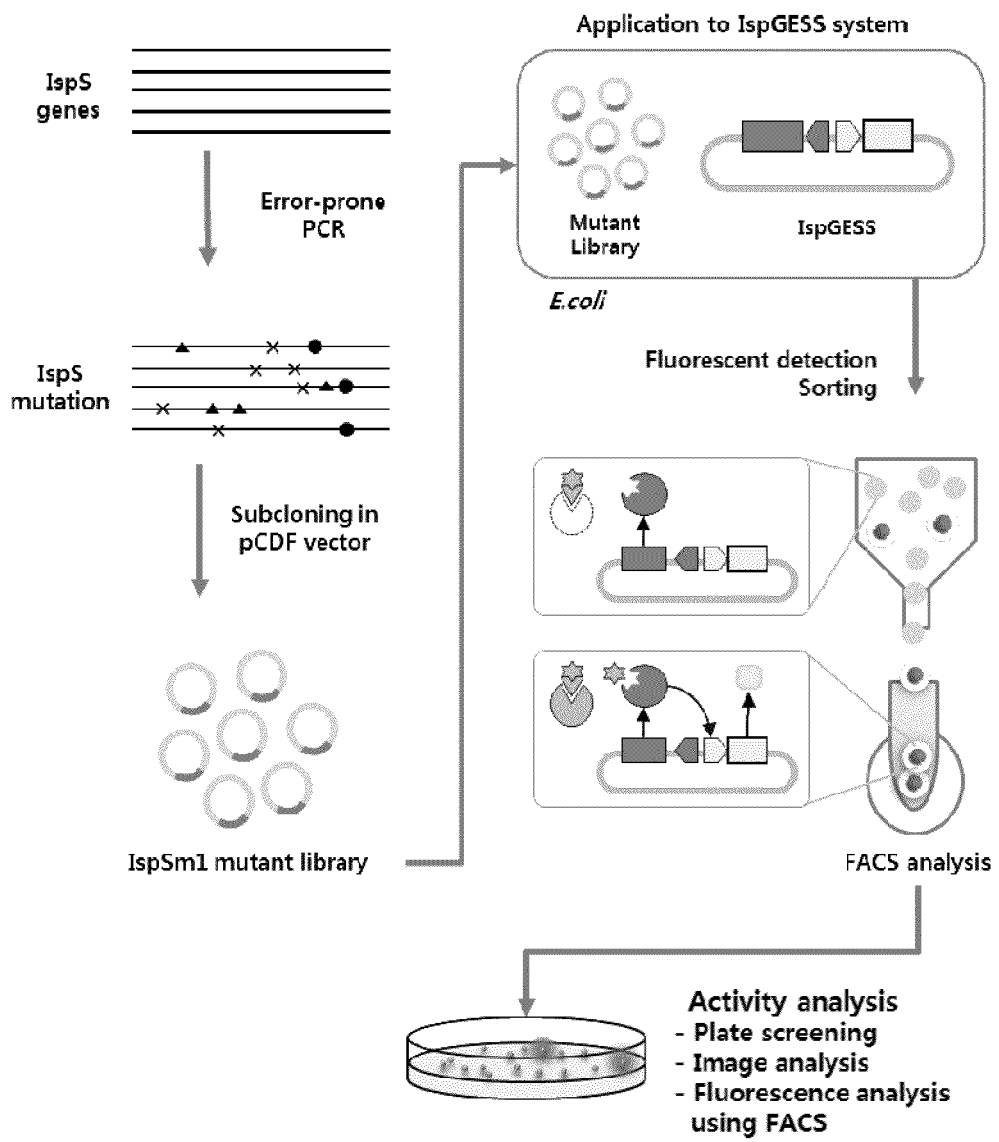
FIG. 5 shows a process of performing high-throughput screening of IspS from a mutant IspSm1 library using the IspGESS.

Using the artificial genetic circuit, a clone having an improved activity was screened from a library of IspSm1 mutants (FIG. 5). First, a large library was constructed using a random mutagenesis kit (Agilent Technologies, USA). PCR was performed using primers of SEQ ID NOS: 5 and 6, and an average of 5 amino acids in the IspSm1 gene was mutated resultantly. Then, the mutated gene was ligated with pCDF vector as described example 3. Ligation mixture was concentrated using Novagen pellet paint (Millipore, USA) and transformed into an *E. coli* DH5a.

SEQ ID NO 5: 5'-cggataacaattcccctgtagaa-3'

SEQ ID NO 6: 5'-tcaagacccgtttagaggcc-3'

As a result, $5 \times 10^5$ of mutant library was constructed. The library cells were recovered, and plasmid DNA was isolated from the cells using a plasmid mini prep kit (Qiagen, Germany). Finally, the mutant library DNA was transformed into *E. coli* BL21(DE3) together with the pIspGESS clone by electroporation. To keep the strain healthy, the strain was allowed to stand at 37° C. for 1 hour. Then, the cells were applied to LB solid medium containing 50 μg/Ml of ampicillin (pIspGESS internal marker) and 10 μg/Ml of streptomycin (IspSm1 internal marker) and were cultured at 37° C. for 16 hours. The number of cell colonies on solid medium was $5 \times 10^5$, and the cell colonies were harvested using storage buffer (1×TY buffer, 15% (v/v) glycerol, 2% (w/v) glucose). In order to obtain IspSm1 mutant having improved activity, $1 \times 10^4$ cells were screened. The library cells were plated on M9 glucose solid medium containing the same amounts of ampicillin and streptomycin as described above and were cultured at 37° C. for 48 hours. With the criterion for screening, cells showing fluorescence intensity which is at least 50% higher than that of IspSm1 were sorted using a FACS-calibur system (Becton Dickinson, USA). Then, 6 clones having higher fluorescence intensity than IspSm1 were isolated.

Figure 6:
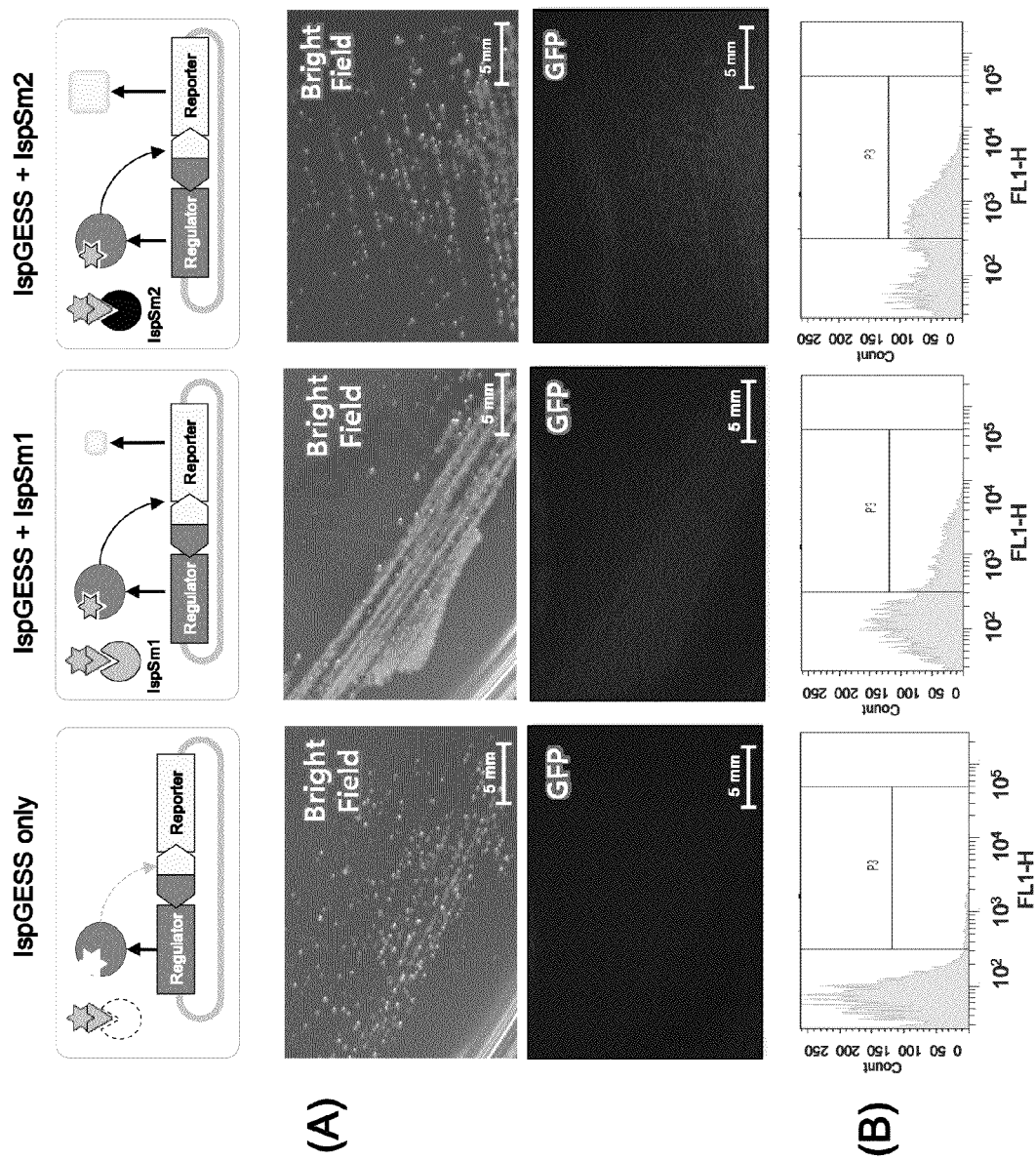
FIG. 6 shows the verification of activity of positive hit (IspSm2) selected from the IspSm1 random mutant library. Three columns represent *E. coli* BL21(DE3) strains containing IspGESS only (left), IspGESS with IspSm1 (center), and IspGESS with IspSm2 (right), respectively. (A) the results of analyzing the fluorescence image of a colony on solid medium; and (B) the results of analyzing the intensity of fluorescence in liquid medium by fluorescence-activated cell sorting (FACS).

The activities of the isolated clones were analyzed by a FACS. As detectors, FSC, SSC, FL1-H (excitation=488 nm, emission=530/30 nm) detectors were set, and 10,000 cells were analyzed. As a result, among the 6 candidates, one mutant-IspSm1 showed two times higher fluorescence intensity than that of IspSm1 (FIG. 6).

The screened mutant IspSm2 was sequenced. The nucleotide sequence of the screened IspSm2 is shown by SEQ ID NO: 7, and the amino acid sequence thereof is shown by SEQ ID NO: 8. For the comparison with IspSm2, the nucleotide sequence is SEQ ID NO: 9, and the amino acid sequence is SEQ ID NO: 10. IspSm1 that ligated in pCDF vector is SEQ ID NO: 11, and IspSm2 that ligated in pCDF vector is SEQ ID NO: 12

In FIG. 7, the amino acid sequence of IspSm2 having increased activity contains a lysine-to-arginine mutation at position 35 of the IspSm1 amino acid sequence.

As a result, it was seen that the constructed system can be applied to the large library where cells having improved enzyme activity could be found.

Example 5

Application of IspGESS with Another Vector System for Isps Expression

For another experiment, using the IspGESS genetic circuit IspS expression vector was changed to pPROLar A122 (clonetech, USA).

First, IspSm1 and IspSm2 genes were amplified using PCR with primers (SEQ ID NOS: 13, 14), and inserted into the NdeI-XbaI restriction enzyme site of a pPROLar vector for pPROLar-ispSm1 and pPROLar-ispSm2 (SEQ ID NOS: 15, 16). Then these two vectors were transformed into an *E. coli* DH5α strain containing IspGESS of Example 1. 50 μg/Ml of ampicillin and 10 μg/Ml of kanamycin were added to LB liquid medium, and *E. coli* cells were cultured with shaking in the LB liquid medium at 37° C. for 16 hours. 4 Ml of the culture medium was placed in a 10 Ml vial and the cultured bacterial strain was then inoculated at a concentration of 1%. Then, the vial was sealed with a septum and the cells were cultured at 28° C. and 200 rpm for 24 hours. The intensity of fluorescence in the cultured cells was analyzed using a FACScalibur system (Becton Dickinson, USA). As detectors, FSC, SSC, and FL1-H (excitation=488 nm, emission=530/30 nm) detectors were set, and 10,000 samples were analyzed.

As a result, it could be observed that the intensity of fluorescence was higher in the cells containing IspSm1 or IspSm2 than in the cells containing neither IspSm1 nor IspSm2 (FIG. 6).

Figure 8:
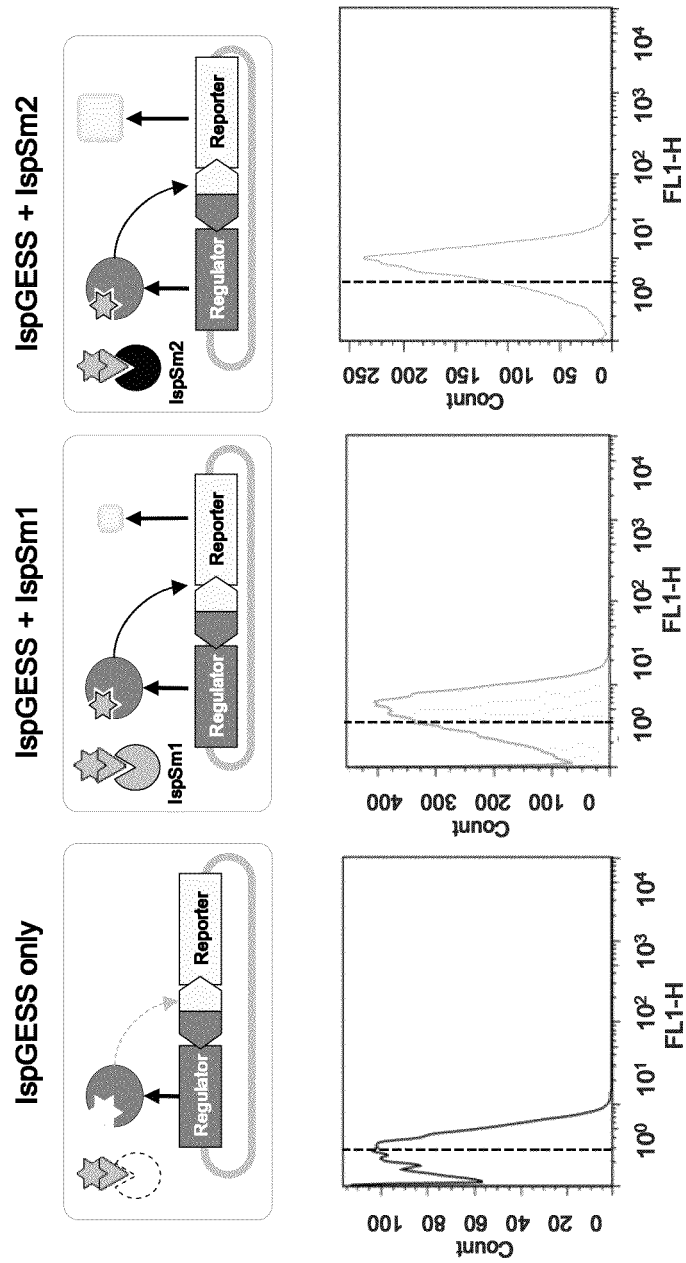
FIG. 8 shows the verification of activity of IspSm1 and IspSm2 in pPROLar vector by fluorescence-activated cell sorting (FACS). Three columns represent *E. coli* DH5a strains containing IspGESS only (left), IspGESS with pPRPLar-IspSm1 (center), and IspGESS with pPRPLar-IspSm2 (right), respectively.
Figure 9:
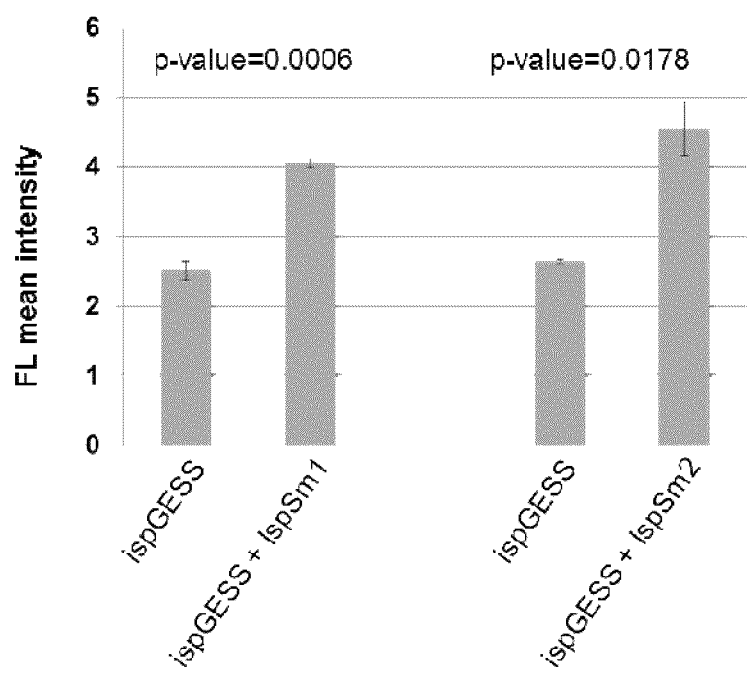
FIG. 9 shows the results of t-test for IspSm1 and IspSm2 activities with respect to no IspS control.

To verify the fluorescence differences of IspSm1, IspSm2 and no IspS induction control, the flow cytometry data was analyzed by t-test. The t-test compared the mean values of the fluorescence signals between the negative control (IspGESS without IspSm1 (IspSm2) induction) and the case that includes IspSm1 (IspSm2) inducer. The result showed a significant difference of their activities (p-value=0.0006 (0.0178)) despite of small replicates. Note that there are three replicates of each case (FIG. 8). Additionally, IspGESS with IspSm2 shows higher fluorescent mean intensity than that of IspGESS with IspSm1.

Example 6

Improved Isoprene Sensitivity by Control of the Regulator Expression

To confirm the sensitivity of the TbuT regulator expression system, we changed the HCE promoter to TRC and ACE promoters, respectively. First, pIspGESS of Example 1 digested by NheI and ClaI restriction enzymes to subclone TRC promoter (SEQ ID NO 17) or ACE promoter (SEQ ID NO 18). Second, TRC or ACE promoter was amplified to ligate into pIspGESS, and also digested by NheI and ClaI restriction enzymes. For the sensing function of pIspGESS-containing recombinant *E. coli*, pIspGESS$_{ACE}$ or pIspGESS$_{TRC}$ was introduced into a single colony of *E. coli* DH5α by heat shock. Then the *E. coli* colony were inoculated into an LB liquid medium (1% (w/v) trypton, 0.5% (w/v) yeast extract, and 1% (w/v) sodium chloride) supplemented with 50 μg/Ml of ampicillin and was cultured with shaking at 37° C. for 14 hours. The culture was inoculated into M9 minimal medium (containing 50 μg/Ml ampicillin, 4% glucose and 1% thiamine) at a concentration of 1% and then cultured with shaking at 37° C. for 6 hours. 100 μM of isoprene was added to each of the test tubes containing the culture broth, after then the culture was incubated with shaking at 27° C. for 18 hours, thereby inducing the expression of fluorescence induced by the isoprene in the culture. The intensity of the intracellular fluorescence was analyzed by a FACS Calibur system (Becton Dickinson, USA). As a detector, a FSC, SSC, FL1-H (excitation=488 nm, emission=530/30 nm) detector was set, and data obtained by observing 10,000 samples were analyzed using CellQuest Pro (Becton Dickinson, USA).

Figure 10:
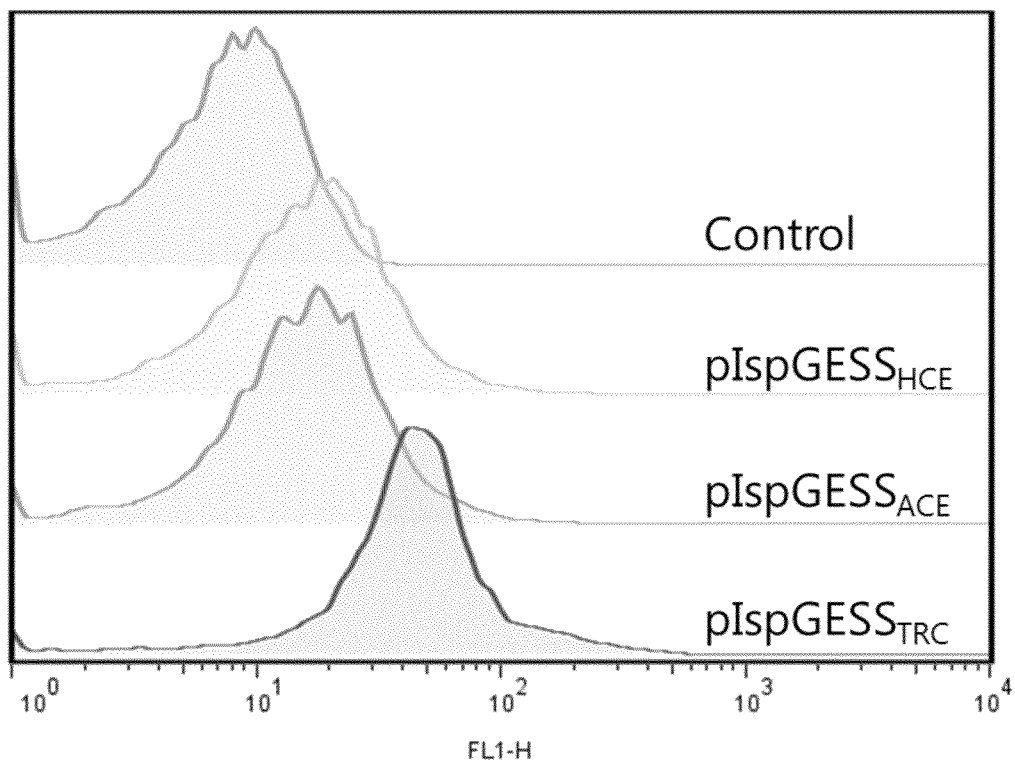
FIG. 10 shows the verification of IspGESS$_{HCE}$ and IspGESS$_{TRC}$ by measuring the responses to isoprene using FACS.

As a result, intensity of reporter for pIspGESS$_{ACE}$ was similar to the pIspGESS$_{HCE}$. However, the reporter intensity of pIspGESS$_{TRC}$ increased 5 times better than the best results achieved with pIspGESS$_{HCE}$ (14.69→82.4) (FIG. 10).

Industrial Applicability

As described above, when the inventive method for screening and quantifying target enzymatic activity is used, the high sensitivity of the genetic circuit to isoprene enables to sense a small amount of isoprene synthase in a single cell rapidly so that it could be possible to find a novel isoprene biosynthesis enzymes from the large library for the efficient and mass production of isoprene. Also the invented method can measure the enzymatic activity quantitatively, which enables to engineering the proteins in MEP/MVA pathway for the improvement of the isoprene production in the microorganism.

More generally, the invention can be advantageously used in the protein engineering technology and large-scale screening for industrially valuable biocatalysts.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of detecting, screening or quantifying the activity of one or more isoprene biosynthesis enzymes using an artificial genetic circuit, the method comprising the steps of:
   (a) providing an artificial genetic circuit for detecting isoprene or microorganisms containing in their chromosomal DNA or cytoplasm an artificial genetic circuit for detecting isoprene, the artificial genetic circuit comprising:
      (i) a gene encoding an isoprene-sensing transcriptional regulator which recognizes isoprene, wherein the gene is obtained by PCR using primers of SEQ ID NO: 1 and SEQ ID NO: 2,
      (ii) at least one reporter gene selected from the group consisting of fluorescence protein-encoding genes and antibiotic resistance genes,
      (iii) a promoter regulating the expression of the isoprene-sensing transcriptional regulator, and
      (iv) a promoter regulating the expression of the reporter gene obtained by PCR using primers of SEQ ID NO: 3 and SEQ ID NO: 4, wherein the promoter regulating the expression of the reporter gene is regulated by the isoprene-sensing transcriptional regulator;
   (b) providing a clone or gene library containing one or more genes encoding an isoprene biosynthesis enzyme;
   (c) introducing the clone or gene library and the artificial genetic circuit for detecting isoprene into host microorganisms to prepare recombinant microorganisms or introducing the clone or gene library into the microorganisms containing the artificial genetic circuit for detecting isoprene to prepare recombinant microorganisms;
   (d) treating the recombinant microorganisms with a compound capable of liberating isoprene by an intracellular enzymatic reaction of the isoprene biosynthesis enzyme; and
   (e) detecting or quantifying the activity of the reporter protein whose expression is induced by sensing isoprene liberated by the intracellular enzymatic reaction of the isoprene biosynthesis enzyme.

2. The method of claim 1, wherein the compound capable of liberating isoprene is selected from the group consisting of dimethylallyl pyrophosphate (DMAPP), methylcyclohexane, heptane, 1-deoxy-D-xylulose 5-phosphate (DXP), 2-C-methyl-D-erythritol 4-phosphate (MEP), 4-(cytidine 5'-diphospho)-2-C-methyl-D-erythritol, 2-phospho-4-(cytidine 5'-di-phospho)-2-C-methyl-D-erythritol (CDP-MEP), 2-C-methyl-D-erythritol 2,4-cyclodiphosphate (ME-cPP), 4-hydroxy-3-methylbut-2-enyl diphosphate (HMBPP), isopentenyl diphosphate (IPP), Acetoacetyl-CoA, HMG-CoA, Mevalonate, phosphomevalonate and diphosphomevalonate.

3. The method of claim 1, wherein the isoprene-sensing transcriptional regulator binds to a region of the promoter regulating the expression of the reporter gene to activate expression of the reporter gene.

4. The method of claim 1, wherein the isoprene biosynthesis enzyme is selected from the group consisting of Isoprene synthase (IspS), DXP synthase (DXS), DXP reductoisomerase (DXR), CDP-ME synthase (MCT), CDP-ME kinase (CMK), ME-cPP synthase (MDS), HMBPP synthase (HDS), HMBPP reductase (HDR), IPP isomerase (IDI), geranyl diphosphate (GPP), geranylgeranyl diphosphate (GGPP), abscisic acid (ABA), atoB/phaA, mvaS, mvaA, mvaK1, mvaK2 and mvaD.

5. The method of claim 1, wherein the fluorescence protein is selected from the group consisting of GFP (green fluorescent protein), EGFP (enhanced green fluorescent protein), GFP$_{UV}$(UV-excited green fluorescent protein), RFP (red fluorescent protein), mRFP (modified red fluorescent protein), YFP (yellow fluorescent protein), mcherry, CFP (cyan fluorescent protein), mGFP (modified green fluorescent protein), ERFP (enhanced red fluorescent protein), BFP (blue fluorescent protein), EBFP (enhanced blue fluorescent protein), EYFP (enhanced yellow fluorescent protein) and ECFP (enhanced cyan fluorescent protein).

6. The method of claim 1, wherein the reporter gene is multiple reporter genes consisting of two or more reporter genes selected from among fluorescence protein-encoding genes and antibiotic resistance genes.

7. The method of claim 1, wherein the antibiotic resistance gene is selected from the group consisting of ampicillin, kanamycin, streptomycin, chloramphenicol and tetracycline.

8. The method of claim 1, wherein the detecting or quantifying the activity of the reporter protein is performed by using a method selected from the group consisting of microcolony image analysis, fluorescence spectrum analysis, fluorescence-activated cell sorting (FACS), and antibiotic resistance measuring method.

9. The method of claim 1, wherein the microorganism is selected from the group consisting of *E. coli*, *Ralstonia*, yeast, plant cells and animal cells.

10. The method of claim 1, wherein the artificial genetic circuit comprises a ribosome binding site (RBS) facilitating the expression of the reporter gene.

11. An artificial genetic circuit for detecting isoprene, the artificial genetic circuit comprising (i) a gene encoding an isoprene-sensing transcriptional regulator which recognizes isoprene liberated from enzymatic reaction of an isoprene biosynthesis enzyme, wherein the gene is obtained by PCR using primers of SEQ ID NO: 1 and SEQ ID NO: 2, (ii) at least one reporter gene selected from the group consisting of fluorescence protein-encoding genes and antibiotic resistance genes, (iii) a promoter regulating the expression of the isoprene-sensing transcriptional regulator, and (iv) a promoter regulating the expression of the reporter gene obtained by PCR using primers of SEQ ID NO: 3 and SEQ ID NO: 4, wherein the promoter regulating the expression of the reporter gene is regulated by the isoprene-sensing transcriptional regulator.

12. A recombinant microorganism containing the artificial genetic circuit of claim 11.

13. A method of quantifying isoprene using an artificial genetic circuit, the method comprising the steps of:
(a) introducing the artificial genetic circuit of claim 11 into host microorganisms to be measured; and
(b) quantifying isoprene by measuring the activity of the reporter protein whose expression is induced by sensing isoprene.

* * * * *

UNITED STATES PATENT AND TRADEMARK OFFICE
CERTIFICATE OF CORRECTION

| | | |
|---|---|---|
| PATENT NO. | : 9,175,330 B2 | Page 1 of 1 |
| APPLICATION NO. | : 13/771952 | |
| DATED | : November 3, 2015 | |
| INVENTOR(S) | : Seung-goo Lee et al. | |

It is certified that error appears in the above-identified patent and that said Letters Patent is hereby corrected as shown below:

IN THE SPECIFICATION

Column 13, line 40: "Example 1 50" should be -- Example 150 --.

Signed and Sealed this
Second Day of February, 2016

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 9,175,330 B2 | |
| APPLICATION NO. | : 13/771952 | |
| DATED | : November 3, 2015 | |
| INVENTOR(S) | : Seung-goo Lee et al. | |

It is certified that error appears in the above-identified patent and that said Letters Patent is hereby corrected as shown below:

IN THE SPECIFICATION

Column 13, line 40: "Example 1 50 µg/Ml of" should be --Example 1. 50 µg/Ml of--.

Signed and Sealed this
Ninth Day of August, 2016

Michelle K. Lee
*Director of the United States Patent and Trademark Office*

SEQUENCE LISTING

```
<160> NUMBER OF SEQ ID NOS: 17

<210> SEQ ID NO 1
<211> LENGTH: 31
<212> TYPE: DNA
<213> ORGANISM: Artificial
<220> FEATURE:
<223> OTHER INFORMATION: primer

<400> SEQUENCE: 1
gccattagat cttcagcttc cgtcgactgg a                                  31

<210> SEQ ID NO 2
<211> LENGTH: 40
<212> TYPE: DNA
<213> ORGANISM: Artificial
<220> FEATURE:
<223> OTHER INFORMATION: primer
```

```
<400> SEQUENCE: 2
gatatcagct agccccttct ggccgcgata agcttgggaa                          40

<210> SEQ ID NO 3
<211> LENGTH: 19
<212> TYPE: DNA
<213> ORGANISM: Artificial
<220> FEATURE:
<223> OTHER INFORMATION: primer

<400> SEQUENCE: 3
attcttacca attgatgaa                                                 19

<210> SEQ ID NO 4
<211> LENGTH: 18
<212> TYPE: DNA
<213> ORGANISM: Artificial
<220> FEATURE:
<223> OTHER INFORMATION: primer

<400> SEQUENCE: 4
cggggtccag ttggtcgt                                                  18

<210> SEQ ID NO 5
<211> LENGTH: 23
<212> TYPE: DNA
<213> ORGANISM: Artificial
<220> FEATURE:
<223> OTHER INFORMATION: primer

<400> SEQUENCE: 5
cggataacaa ttcccctgta gaa                                            23

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
tcaagacccg tttagaggcc                                                20

<210> SEQ ID NO 7
<211> LENGTH: 1683
<212> TYPE: DNA
<213> ORGANISM: Artificial
<220> FEATURE:
<223> OTHER INFORMATION: IspSm2

<400> SEQUENCE: 7
atggcttgct ctgtatccac tgagaacgta tctttcactg agactgaaac tgagacccgt    60
cgctctgcga actatgagcc aaactcttgg gattacgatt atcggctgtc ctctgacact   120
gacgaaagca ttgaagttta caaggacaaa gcgaaaaagc tggaagcgga ggttcgtcgc   180
gaaatcaaca acgagaaagc tgaattcctg actctgctgg agctgatcga caacgtacag   240
cgtctgggtc tgggttaccg tttcgagtct gacatccgcc gtgctctgga tcgcttcgtt   300
tccagcggcg gtttcgatgc agtgaccaag actagcctgc atgcgaccgc gctgtctttc   360
cgtctgctgc gtcagcacgg ttttgaagtt tctcaggaag cgttctctgg cttcaaggac   420
cagaacggta atttcctgga aaacctgaag gaggacatta aggcgattct gtccctgtac   480
```

```
gaagcgtctt ttctggcgct ggaaggcgag aacatcctgg acgaagcgaa agtattcgca    540
atctcccacc tgaaagaact gagcgaagaa aaaatcggta agatctggc ggaacaggtg     600 aaccacgctc tggaactgcc tctgcatcgt cgtacccagc gtctggaggc tgtgctgtcc    660
attgaagcat accgtaagaa agaagatgca gatcaggttc tgctggaact ggcgatcctg    720
gactacaaca tgattcagtc tgtgtaccag cgtgacctgc gtgaaacctc cgctggtgg    780 cgccgtgtgg gtctggcaac caaactgcac ttcgcacgcg atcgtctgat tgaatccttc    840
tactgggctg taggcgtggc cttcgaaccg cagtactccg attgccgtaa ctctgttgct    900
aaaatgttct ctttcgttac cattatcgat gacatctatg acgtttatgg tacccctggat  960 gaactggagc tgttcaccaa cgcagttgaa cgctgggacg ttaacgcgat tgatgacctg    1020
cctgactaca tgaaactgtg cttcctggcg ctgtataaca ctatcaacga atcgcgtat    1080 gataacctga agaaaaagg tgaaaacatt ctgccgtatc tgaccaaagc ctgggccgac    1140
ctgtgtaacg cattcctgca ggaggccaaa tggctgtaca ataagtctac tcctactttc    1200
gacgattact tcggtaacgc ttggaaatct agctctggcc cgctgcaact ggtcttcgcc    1260
tatttcgcgg tagtgcaaaa catcaaaaag gaagagatcg agaatctgca gaaatatcac    1320
gacattatct cccgcccgag ccacatcttc cgcctgtgta cgacctggc ctccgcatcc    1380 gcagaaattg cacgcggcga aaccgccaac tccgtatcct gctatatgcg taccaaaggc    1440
atcagcgaag aactggctac cgaatccgtg atgaacctga tcgatgaaac ttggaagaag    1500
atgaacaaag aaaaactggg cggttctctg ttcgccaaac cattcgttga accgcgatt    1560 aacctggcgc gccaatctca ctgcacctat cataacggtg acgcacacac ctccccggat    1620
gaactgaccc gtaagcgtgt gctgtccgtt attaccgaac caattctgcc gttcgaacgc    1680
taa                                                                 1683
```

<210> SEQ ID NO 8
<211> LENGTH: 560
<212> TYPE: PRT
<213> ORGANISM: Artificial
<220> FEATURE:
<223> OTHER INFORMATION: IspSm2

<400> SEQUENCE: 8

```
Met Ala Cys Ser Val Ser Thr Glu Asn Val Ser Phe Thr Glu Thr Glu
1               5                   10                  15

Thr Glu Thr Arg Arg Ser Ala Asn Tyr Glu Pro Asn Ser Trp Asp Tyr
                20                  25                  30

Asp Tyr Arg Leu Ser Ser Asp Thr Asp Glu Ser Ile Glu Val Tyr Lys
            35                  40                  45

Asp Lys Ala Lys Lys Leu Glu Ala Glu Val Arg Arg Glu Ile Asn Asn
        50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Arg Ala Leu
                85                  90                  95

Asp Arg Phe Val Ser Ser Gly Gly Phe Asp Ala Val Thr Lys Thr Ser
            100                 105                 110

Leu His Ala Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140
```

```
Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
            165                 170                 175

Lys Val Phe Ala Ile Ser His Leu Lys Glu Leu Ser Glu Glu Lys Ile
            180                 185                 190

Gly Lys Asp Leu Ala Glu Gln Val Asn His Ala Leu Glu Leu Pro Leu
            195                 200                 205

His Arg Arg Thr Gln Arg Leu Glu Ala Val Leu Ser Ile Glu Ala Tyr
210                 215                 220

Arg Lys Lys Glu Asp Ala Asp Gln Val Leu Leu Glu Leu Ala Ile Leu
225                 230                 235                 240

Asp Tyr Asn Met Ile Gln Ser Val Tyr Gln Arg Asp Leu Arg Glu Thr
            245                 250                 255

Ser Arg Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
            275                 280                 285

Glu Pro Gln Tyr Ser Asp Cys Arg Asn Ser Val Ala Lys Met Phe Ser
            290                 295                 300

Phe Val Thr Ile Ile Asp Asp Ile Tyr Asp Val Tyr Gly Thr Leu Asp
305                 310                 315                 320

Glu Leu Glu Leu Phe Thr Asn Ala Val Glu Arg Trp Asp Val Asn Ala
                325                 330                 335

Ile Asp Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Glu Lys Gly Glu
            355                 360                 365

Asn Ile Leu Pro Tyr Leu Thr Lys Ala Trp Ala Asp Leu Cys Asn Ala
            370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Gly Pro Leu Gln
            405                 410                 415

Leu Val Phe Ala Tyr Phe Ala Val Val Gln Asn Ile Lys Lys Glu Glu
            420                 425                 430

Ile Glu Asn Leu Gln Lys Tyr His Asp Ile Ile Ser Arg Pro Ser His
            435                 440                 445

Ile Phe Arg Leu Cys Asn Asp Leu Ala Ser Ala Ser Ala Glu Ile Ala
450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
            485                 490                 495

Thr Trp Lys Lys Met Asn Lys Glu Lys Leu Gly Gly Ser Leu Phe Ala
            500                 505                 510

Lys Pro Phe Val Glu Thr Ala Ile Asn Leu Ala Arg Gln Ser His Cys
            515                 520                 525

Thr Tyr His Asn Gly Asp Ala His Thr Ser Pro Asp Glu Leu Thr Arg
            530                 535                 540

Lys Arg Val Leu Ser Val Ile Thr Glu Pro Ile Leu Pro Phe Glu Arg
545                 550                 555                 560
```

<210> SEQ ID NO 9
<211> LENGTH: 1683
<212> TYPE: DNA
<213> ORGANISM: Artificial
<220> FEATURE:
<223> OTHER INFORMATION: P. trichocarpa-derived IspS (IspSm1)

<400> SEQUENCE: 9

```
atggcttgct ctgtatccac tgagaacgta tctttcactg agactgaaac tgagacccgt      60
cgctctgcga actatgagcc aaactcttgg gattacgatt atctgctgtc ctctgacact     120
gacgaaagca ttgaagttta caaggacaaa gcgaaaaagc tggaagcgga ggttcgtcgc     180
gaaatcaaca acgagaaagc tgaattcctg actctgctgg agctgatcga caacgtacag     240
cgtctgggtc tgggttaccg tttcgagtct gacatccgcc gtgctctgga tcgcttcgtt     300
tccagcggcg gtttcgatgc agtgaccaag actagcctgc atgcgaccgc gctgtctttc     360
cgtctgctgc gtcagcacgg ttttgaagtt tctcaggaag cgttctctgg cttcaaggac     420
cagaacggta tttcctgga aaacctgaag gaggacatta aggcgattct gtccctgtac     480
gaagcgtctt ttctggcgct ggaaggcgag aacatcctgg acgaagcgaa agtattcgca     540
atctcccacc tgaaagaact gagcgaagaa aaatcggta agatctggc ggaacaggtg      600
aaccacgctc tggaactgcc tctgcatcgt cgtacccagc gtctggaggc tgtgctgtcc     660
attgaagcat accgtaagaa agaagatgca gatcaggttc tgctggaact ggcgatcctg     720
gactacaaca tgattcagtc tgtgtaccag cgtgacctgc gtgaaacctc tcgctggtgg     780
cgccgtgtgg gtctggcaac caaactgcac ttcgcacgcg atcgtctgat tgaatccttc     840
tactgggctg taggcgtggc cttcgaaccg cagtactccg attgccgtaa ctctgttgct     900
aaaatgttct ctttcgttac cattatcgat gacatctatg acgtttatgg taccctggat     960
gaactggagc tgttcaccaa cgcagttgaa cgctgggacg ttaacgcgat tgatgacctg    1020
cctgactaca tgaaactgtg cttcctggcg ctgtataaca ctatcaacga gatcgcgtat    1080
gataacctga agaaaaagg tgaaaacatt ctgccgtatc tgaccaaagc ctgggccgac    1140
ctgtgtaacg cattcctgca ggaggccaaa tggctgtaca ataagtctac tcctactttc    1200
gacgattact tcggtaacgc tttggaaatct agctctggcc gctgcaact ggtcttcgcc     1260
tatttcgcgg tagtgcaaaa catcaaaaag gaagagatcg agaatctgca gaaatatcac    1320
gacattatct cccgcccgag ccacatcttc cgcctgtgta acgacctggc ctccgcatcc    1380
gcagaaattg cacgcggcga aaccgccaac tccgtatcct gctatatgcg taccaaaggc    1440
atcagcgaag aactggctac cgaatccgtg atgaacctga tcgatgaaac ttggaagaag    1500
atgaacaaag aaaaactggg cggttctctg ttcgccaaac cattcgttga accgcgatt    1560
aacctggcgc gccaatctca ctgcacctat cataacggtg acgcacacac ctccccggat    1620
gaactgaccc gtaagcgtgt gctgtccgtt attaccgaac caattctgcc gttcgaacgc    1680
taa                                                                   1683
```

<210> SEQ ID NO 10
<211> LENGTH: 5120
<212> TYPE: DNA
<213> ORGANISM: Artificial
<220> FEATURE:
<223> OTHER INFORMATION: pCDF-IspSm1

<400> SEQUENCE: 10

```
ggggaattgt gagcggataa caattcccct gtagaaataa ttttgtttaa ctttaataag      60
```

```
gagatatacc atggcttgct ctgtatccac tgagaacgta tctttcactg agactgaaac    120
tgagacccgt cgctctgcga actatgagcc aaactcttgg gattacgatt atctgctgtc    180
ctctgacact gacgaaagca ttgaagttta caaggacaaa gcgaaaaagc tggaagcgga    240
ggttcgtcgc gaaatcaaca cgagaaagc tgaattcctg actctgctgg agctgatcga    300
caacgtacag cgtctgggtc tgggttaccg tttcgagtct gacatccgcc gtgctctgga    360
tcgcttcgtt tccagcggcg gtttcgatgc agtgaccaag actagcctgc atgcgaccgc    420
gctgtctttc cgtctgctgc gtcagcacgg ttttgaagtt tctcaggaag cgttctctgg    480
cttcaaggac cagaacggta atttcctgga aaacctgaag gaggacatta aggcgattct    540
gtccctgtac gaagcgtctt ttctggcgct ggaaggcgag aacatcctgg acgaagcgaa    600
agtattcgca atctcccacc tgaaagaact gagcgaagaa aaaatcggta agatctggc    660 ggaacaggtg aaccacgctc tggaactgcc tctgcatcgt cgtacccagc gtctggaggc    720
tgtgctgtcc attgaagcat accgtaagaa agaagatgca gatcaggttc tgctggaact    780
ggcgatcctg gactacaaca tgattcagtc tgtgtaccag cgtgacctgc gtgaaacctc    840
tcgctggtgg cgccgtgtgg gtctggcaac caaactgcac ttcgcacgcg atcgtctgat    900
tgaatccttc tactgggctg taggcgtggc cttcgaaccg cagtactccg attgccgtaa    960
ctctgttgct aaaatgttct ctttcgttac cattatcgat gacatctatg acgtttatgg   1020
taccctggat gaactggagc tgttcaccaa cgcagttgaa cgctgggacg ttaacgcgat   1080
tgatgacctg cctgactaca tgaaactgtg cttcctggcg ctgtataaca ctatcaacga   1140
gatcgcgtat gataacctga agaaaaagg tgaaaacatt ctgccgtatc tgaccaaagc   1200
ctgggccgac ctgtgtaacg cattcctgca ggaggccaaa tggctgtaca ataagtctac   1260
tcctactttc gacgattact cggtaacgc ttggaaatct agctctggcc cgctgcaact   1320
ggtcttcgcc tatttcgcgg tagtgcaaaa catcaaaaag aagagatcg agaatctgca   1380 gaaatatcac gacattatct cccgcccgag ccacatcttc cgcctgtgta acgacctggc   1440
ctccgcatcc gcagaaattg cacgcggcga aaccgccaac tccgtatcct gctatatgcg   1500
taccaaaggc atcagcgaag aactggctac cgaatccgtg atgaacctga tcgatgaaac   1560
ttggaagaag atgaacaaag aaaaactggg cggttctctg ttcgccaaac cattcgttga   1620
aaccgcgatt aacctggcgc gccaatctca ctgcacctat cataacggtg acgcacacac   1680
ctccccggat gaactgaccc gtaagcgtgt gctgtccgtt attaccgaac caattctgcc   1740
gttcgaacgc caccaccacc accaccacta acctaggctg ctgccaccgc tgagcaataa   1800
ctagcataac cccttggggc ctctaaacgg gtcttgaggg gttttttgct gaaacctcag   1860
gcatttgaga agcacacggt cacactgctt ccggtagtca ataaaccggt aaaccagcaa   1920
tagacataag cggctattta cgaccctgc cctgaaccga cgaccgggtc atcgtggccg   1980
gatcttgcgg cccctcggct tgaacgaatt gttagacatt atttgccgac taccttggtg   2040
atctcgcctt tcacgtagtg gacaaattct tccaactgat ctgcgcgcga ggccaagcga   2100
tcttcttctt gtccaagata agcctgtcta gcttcaagta tgacgggctg atactgggcc   2160
ggcaggcgct ccattgccca gtcggcagcg acatccttcg cgcgatttt gccggttact   2220 gcgctgtacc aaatgcggga caacgtaagc actacatttc gctcatcgcc agcccagtcg   2280 gcggcgagt tccatagcgt taaggtttca tttagcgcct caaatagatc ctgttcagga   2340 accgatcaa agagttcctc cgccgctgga cctaccaagg caacgctatg ttctcttgct   2400
tttgtcagca agatagccag atcaatgtcg atcgtggctg gctcgaagat acctgcaaga   2460
```

```
atgtcattgc gctgccattc tccaaattgc agttcgcgct tagctggata acgccacgga    2520
atgatgtcgt cgtgcacaac aatggtgact tctacagcgc ggagaatctc gctctctcca    2580
ggggaagccg aagtttccaa aaggtcgttg atcaaagctc gccgcgttgt ttcatcaagc    2640
cttacggtca ccgtaaccag caaatcaata tcactgtgtg gcttcaggcc gccatccact    2700
gcggagccgt acaaatgtac ggccagcaac gtcggttcga gatggcgctc gatgacgcca    2760
actacctctg atagttgagt cgatacttcg gcgatcaccg cttccctcat actcttcctt    2820
tttcaatatt attgaagcat ttatcagggt tattgtctca tgagcggata catatttgaa    2880
tgtatttaga aaaataaaca aatagctagc tcactcggtc gctacgctcc gggcgtgaga    2940
ctgcggcggg cgctgcggac acatacaaag ttacccacag attccgtgga taagcagggg    3000
actaacatgt gaggcaaaac agcagggccg cgccggtggc gttttccat aggctccgcc     3060
ctcctgccag agttcacata aacagacgct tttccggtgc atctgtggga gccgtgaggc    3120
tcaaccatga atctgacagt acgggcgaaa cccgacagga cttaaagatc cccaccgttt    3180
ccggcgggtc gctccctctt gcgctctcct gttccgaccc tgccgtttac cggatacctg    3240
ttccgccttt ctcccttacg ggaagtgtgg cgctttctca tagctcacac actggtatct    3300
cggctcggtg taggtcgttc gctccaagct gggctgtaag caagaactcc ccgttcagcc    3360
cgactgctgc gccttatccg gtaactgttc acttgagtcc aacccggaaa agcacggtaa    3420
aacgccactg gcagcagcca ttggtaactg ggagttcgca gaggatttgt ttagctaaac    3480
acgcggttgc tcttgaagtg tgcgccaaag tccggctaca ctggaaggac agatttggtt    3540
gctgtgctct gcgaaagcca gttaccacgg ttaagcagtt ccccaactga cttaaccttc    3600
gatcaaacca cctccccagg tggttttttc gtttacaggg caaaagatta cgcgcagaaa    3660
aaaaggatct caagaagatc ctttgatctt ttctactgaa ccgctctaga tttcagtgca    3720
atttatctct tcaaatgtag cacctgaagt cagccccata cgatataagt tgtaattctc    3780
atgttagtca tgccccgcgc ccaccggaag gagctgactg ggttgaaggc tctcaagggc    3840
atcggtcgag atcccggtgc ctaatgagtg agctaactta cattaattgc gttgcgctca    3900
ctgcccgctt tccagtcggg aaacctgtcg tgccagctgc attaatgaat cggccaacgc    3960
gcggggagag gcggtttgcg tattgggcgc cagggtggtt tttcttttca ccagtgagac    4020
gggcaacagc tgattgccct tcaccgcctg gccctgagag agttgcagca agcggtccac    4080
gctggtttgc cccagcaggc gaaaatcctg tttgatggtg gttaacggcg ggatataaca    4140
tgagctgtct tcggtatcgt cgtatcccac taccgagatg tccgcaccaa cgcgcagccc    4200
ggactcggta atggcgcgca ttgcgcccag cgccatctga tcgttggcaa ccagcatcgc    4260
agtgggaacg atgccctcat tcagcatttg catggtttgt tgaaaaccgg acatggcact    4320
ccagtcgcct tcccgttccg ctatcggctg aatttgattg cgagtgagat atttatgcca    4380
gccagccaga cgcagacgcg ccgagacaga acttaatggg cccgctaaca gcgcgatttg    4440
ctggtgaccc aatgcgacca gatgctccac gcccagtcgc gtaccgtctt catgggagaa    4500
aataatactg ttgatgggtg tctggtcaga gacatcaaga ataacgccg gaacattagt     4560
gcaggcagct tccacagcaa tggcatcctg gtcatccagc ggatagttaa tgatcagccc    4620
actgacgcgt tgcgcgagaa gattgtgcac cgccgcttta caggcttcga cgccgcttcg    4680
ttctaccatc gacaccacca cgctggcacc cagttgatcg cgcgagatt taatcgccgc     4740
gacaatttgc gacggcgcgt gcagggccag actggaggtg caacgccaa tcagcaacga     4800
```

-continued

```
ctgtttgccc gccagttgtt gtgccacgcg gttgggaatg taattcagct ccgccatcgc    4860
cgcttccact ttttcccgcg ttttcgcaga aacgtggctg gcctggttca ccacgcggga    4920
aacggtctga taagagacac cggcatactc tgcgacatcg tataacgtta ctggtttcac    4980
attcaccacc ctgaattgac tctcttccgg gcgctatcat gccataccgc gaaaggtttt    5040
gcgccattcg atggtgtccg ggatctcgac gctctccctt atgcgactcc tgcattagga    5100
aattaatacg actcactata                                                5120
```

<210> SEQ ID NO 11
<211> LENGTH: 5120
<212> TYPE: DNA
<213> ORGANISM: Artificial
<220> FEATURE:
<223> OTHER INFORMATION: pCDF-IspSm2

<400> SEQUENCE: 11

```
ggggaattgt gagcggataa caattcccct gtagaaataa ttttgtttaa ctttaataag      60
gagatatacc atggcttgct ctgtatccac tgagaacgta tctttcactg agactgaaac     120
tgagacccgt cgctctgcga actatgagcc aaactcttgg gattacgatt atctgctgtc     180
ctctgacact gacgaaagca ttgaagttta caggacaaa gcgaaaaagc tggaagcgga     240
ggttcgtcgc gaaatcaaca cgagaaaagc tgaattccgg actctgctgg agctgatcga     300
caacgtacag cgtctgggtc tgggttaccg tttcgagtct gacatccgcc gtgctctgga     360
tcgcttcgtt tccagcggcg gtttcgatgc agtgaccaag actagcctgc atgcgaccgc     420
gctgtctttc cgtctgctgc gtcagcacgg ttttgaagtt tctcaggaag cgttctctgg     480
cttcaaggac cagaacggta atttcctgga aaacctgaag gaggacatta aggcgattct     540
gtccctgtac gaagcgtctt ttctggcgct ggaaggcgag aacatcctgg acgaagcgaa     600
agtattcgca atctcccacc tgaaagaact gagcgaagaa aaaatcggta agatctggc     660
ggaacaggtg aaccacgctc tggaactgcc tctgcatcgt cgtacccagc gtctggaggc     720
tgtgctgtcc attgaagcat accgtaagaa agaagatgca gatcaggttc tgctggaact     780
ggcgatcctg gactacaaca tgattcagtc tgtgtaccag cgtgacctgc gtgaaacctc     840
tcgctggtgg cgccgtgtgg gtctggcaac caaactgcac ttcgcacgcg atcgtctgat     900
tgaatccttc tactgggctg taggcgtggc cttcgaaccg cagtactccg attgccgtaa     960
ctctgttgct aaaatgttct ctttcgttac cattatcgat gacatctatg acgtttatgg    1020
taccctggat gaactggagc tgttcaccaa cgcagttgaa cgctgggacg ttaacgcgat    1080
tgatgacctg cctgactaca tgaaactgtg cttcctggcg ctgtataaca ctatcaacga    1140
gatcgcgtat gataacctga agaaaaaggt gaaaacatt ctgccgtatc tgaccaaagc    1200
ctgggccgac ctgtgtaacg cattcctgca ggaggccaaa tggctgtaca ataagtctac    1260
tcctactttc gacgattact cggtaacgc ttggaaatct agctctgcc cgctgcaact    1320
ggtcttcgcc tatttcgcgg tagtgcaaaa catcaaaaag gaagagatcg agaatctgca    1380
gaaatatcac gacattatct cccgcccgag ccacatcttc cgcctgtgta cgacctggc    1440
ctccgcatcc gcagaaattg cacgcggcga accgccaac tccgtatcct gctatatgcg    1500
taccaaaggc atcagcgaag aactggctac cgaatccgtg atgaacctga tcgatgaaac    1560
ttggaagaag atgaacaaag aaaactggg cggttctctg ttcgccaaac cattcgttga    1620
aaccgcgatt aacctggcgc gccaatctca ctgcacctat cataacggtg acgcacacac    1680
ctccccggat gaactgaccc gtaagcgtgt gctgtccgtt attaccgaac caattctgcc    1740
```

```
gttcgaacgc caccaccacc accaccacta acctaggctg ctgccaccgc tgagcaataa    1800
ctagcataac cccttggggc ctctaaacgg gtcttgaggg gttttttgct gaaacctcag    1860
gcatttgaga agcacacggt cacactgctt ccggtagtca ataaaccggt aaaccagcaa    1920
tagacataag cggctattta acgaccctgc cctgaaccga cgaccgggtc atcgtggccg    1980
gatcttgcgg cccctcggct tgaacgaatt gttagacatt atttgccgac taccttggtg    2040
atctcgcctt tcacgtagtg gacaaattct tccaactgat ctgcgcgcga ggccaagcga    2100
tcttcttctt gtccaagata agcctgtcta gcttcaagta tgacgggctg atactgggcc    2160
ggcaggcgct ccattgccca gtcggcagcg acatccttcg gcgcgatttt gccggttact    2220
gcgctgtacc aaatgcggga caacgtaagc actacatttc gctcatcgcc agcccagtcg    2280
ggcggcgagt tccatagcgt taaggtttca tttagcgcct caaatagatc ctgttcagga    2340
accggatcaa agagttcctc cgccgctgga cctaccaagg caacgctatg ttctcttgct    2400
tttgtcagca agatagccag atcaatgtcg atcgtggctg gctcgaagat acctgcaaga    2460
atgtcattgc gctgccattc tccaaattgc agttcgcgct tagctggata acgccacgga    2520
atgatgtcgt cgtgcacaac aatggtgact tctacagcgc ggagaatctc gctctctcca    2580
ggggaagccg aagtttccaa aaggtcgttg atcaaagctc gccgcgttgt tcatcaagc     2640
cttacggtca ccgtaaccag caaatcaata tcactgtgtg gcttcaggcc gccatccact    2700
gcggagccgt acaaatgtac ggccagcaac gtcggttcga gatggcgctc gatgacgcca    2760
actacctctg atagttgagt cgatacttcg gcgataccg cttccctcat actcttcctt      2820
tttcaatatt attgaagcat ttatcagggt tattgtctca tgagcggata catatttgaa    2880
tgtatttaga aaaataaaca aatagctagc tcactcggtc gctacgctcc gggcgtgaga    2940
ctgcggcggg cgctgcggac acatacaaag ttacccacag attccgtgga taagcagggg    3000
actaacatgt gaggcaaaac agcagggccg cgccggtggc gttttccat aggctccgcc      3060
ctcctgccag agttcacata aacagacgct tttccggtgc atctgtggga gccgtgaggc    3120
tcaaccatga atctgacagt acgggcgaaa cccgacagga cttaaagatc cccaccgttt    3180
ccggcgggtc gctccctctt gcgctctcct gttccgaccc tgccgtttac cggataccctg   3240
ttccgccttt ctcccttacg ggaagtgtgg cgctttctca tagctcacac actggtatct    3300
cggctcggtg taggtcgttc gctccaagct gggctgtaag caagaactcc ccgttcagcc    3360
cgactgctgc gccttatccg gtaactgttc acttgagtcc aacccggaaa agcacggtaa    3420
aacgccactg gcagcagcca ttggtaactg ggagttcgca gaggatttgt ttagctaaac    3480
acgcggttgc tcttgaagtg tgcgccaaag tccggctaca ctggaaggac agatttggtt    3540
gctgtgctct gcgaaagcca gttaccacgg ttaagcagtt ccccaactga cttaaccttc    3600
gatcaaacca cctccccagg tggttttttc gtttacaggg caaaagatta cgcgcagaaa    3660
aaaaggatct caagaagatc ctttgatctt ttctactgaa ccgctctaga tttcagtgca    3720
atttatctct tcaaatgtag cacctgaagt cagccccata cgatataagt tgtaattctc    3780
atgttagtca tgccccgcgc ccaccggaag gagctgactg ggttgaaggc tctcaagggc    3840
atcggtcgag atcccggtgc ctaatgagtg agctaactta cattaattgc gttgcgctca    3900
ctgcccgctt tccagtcggg aaacctgtcg tgccagctgc attaatgaat cggccaacgc    3960
gcggggagag gcggtttgcg tattgggcgc cagggtggtt tttcttttca ccagtgagac    4020
gggcaacagc tgattgccct tcaccgcctg gccctgagag agttgcagca agcggtccac    4080
```

```
gctggtttgc cccagcaggc gaaaatcctg tttgatggtg gttaacggcg ggatataaca    4140
tgagctgtct tcggtatcgt cgtatcccac taccgagatg tccgcaccaa cgcgcagccc    4200
ggactcggta atggcgcgca ttgcgcccag cgccatctga tcgttggcaa ccagcatcgc    4260
agtgggaacg atgccctcat tcagcatttg catggtttgt tgaaaaccgg acatggcact    4320
ccagtcgcct tcccgttccg ctatcggctg aatttgattg cgagtgagat atttatgcca    4380
gccagccaga cgcagacgcg ccagacagaa cttaatgggc ccgctaaca gcgcgatttg     4440
ctggtgaccc aatgcgacca gatgctccac gcccagtcgc gtaccgtctt catgggagaa    4500
aataatactg ttgatgggtg tctggtcaga gacatcaaga ataacgccg gaacattagt     4560
gcaggcagct tccacagcaa tggcatcctg gtcatccagc ggatagttaa tgatcagccc    4620
actgacgcgt tgcgcgagaa gattgtgcac cgccgcttta caggcttcga cgccgcttcg    4680
ttctaccatc gacaccacca cgctggcacc cagttgatcg gcgcgagatt taatcgccgc    4740
gacaatttgc gacggcgcgt gcagggccag actggaggtg gcaacgccaa tcagcaacga    4800
ctgtttgccc gccagttgtt gtgccacgcg gttgggaatg taattcagct ccgccatcgc    4860
cgcttccact ttttcccgcg ttttcgcaga acgtggctg gcctggttca ccacgcggga     4920
aacggtctga taagagacac cggcatactc tgcgacatcg tataacgtta ctggtttcac    4980
attcaccacc ctgaattgac tctcttccgg gcgctatcat gccataccgc gaaaggtttt    5040
gcgccattcg atggtgtccg ggatctcgac gctctccctt atgcgactcc tgcattagga    5100
aattaatacg actcactata                                                5120

<210> SEQ ID NO 12
<211> LENGTH: 31
<212> TYPE: DNA
<213> ORGANISM: Artificial
<220> FEATURE:
<223> OTHER INFORMATION: (Xba)PtispS-R primer

<400> SEQUENCE: 12
ctagtctaga ttagcgttcg aacggcagaa t                                    31

<210> SEQ ID NO 13
<211> LENGTH: 33
<212> TYPE: DNA
<213> ORGANISM: Artificial
<220> FEATURE:
<223> OTHER INFORMATION: (Nde)PtispS-F primer

<400> SEQUENCE: 13
gggaattcca tatggcttgc tctgtatcca ctg                                  33

<210> SEQ ID NO 14
<211> LENGTH: 4194
<212> TYPE: DNA
<213> ORGANISM: Artificial
<220> FEATURE:
<223> OTHER INFORMATION: pPROLar-IspSm1

<400> SEQUENCE: 14
tcgagcatag catttttatc cataagatta gcggatctaa cctttacaat tgtgagcgct      60
cacaattatg atagattcaa ttgtgagcgg ataacaattt cacacagaat tcattaaaga    120
ggagaaaggt accccatatg gcttgctctg tatccactga gaacgtatct ttcactgaga    180
ctgaaactga gacccgtcgc tctgcgaact atgagccaaa ctcttgggat tacgattatc    240
tgctgtcctc tgacactgac gaaagcattg aagtttacaa ggacaaagcg aaaaagctgg    300
```

```
aagcggaggt tcgtcgcgaa atcaacaacg agaaagctga attcctgact ctgctggagc    360
tgatcgacaa cgtacagcgt ctgggtctgg gttaccgttt cgagtctgac atccgccgtg    420
ctctggatcg cttcgtttcc agcggcggtt tcgatgcagt gaccaagact agcctgcatg    480
cgaccgcgct gtctttccgt ctgctgcgtc agcacggttt tgaagtttct caggaagcgt    540
tctctggctt caaggaccag aacggtaatt tcctggaaaa cctgaaggag acattaagg     600 cgattctgtc cctgtacgaa gcgtcttttc tggcgctgga aggcgagaac atcctggacg    660
aagcgaaagt attcgcaatc tcccacctga agaactgag cgaagaaaaa atcggtaaag     720
atctggcgga acaggtgaac cacgctctgg aactgcctct gcatcgtcgt acccagcgtc    780
tggaggctgt gctgtccatt gaagcatacc gtaagaaaga agatgcagat caggttctgc    840
tggaactggc gatcctggac tacaacatga ttcagtctgt gtaccagcgt gacctgcgtg    900
aaacctctcg ctggtggcgc cgtgtgggtc tggcaaccaa actgcacttc gcacgcgatc    960
gtctgattga atccttctac tgggctgtag gcgtggcctt cgaaccgcag tactccgatt   1020
gccgtaactc tgttgctaaa atgttctctt tcgttaccat tatcgatgac atctatgacg   1080
tttatggtac cctggatgaa ctggagctgt tcaccaacgc agttgaacgc tgggacgtta   1140
acgcgattga tgacctgcct gactacatga aactgtgctt cctggcgctg tataacacta   1200
tcaacgagat cgcgtatgat aacctgaaag aaaaaggtga aaacattctg ccgtatctga   1260
ccaaagcctg ggccgacctg tgtaacgcat tcctgcagga ggccaaatgg ctgtacaata   1320
agtctactcc tactttcgac gattacttcg gtaacgcttg gaaatctagc tctggcccgc   1380
tgcaactggt cttcgcctat ttcgcggtag tgcaaaacat caaaaaggaa gagatcgaga   1440
atctgcagaa atatcacgac attatctccc gcccgagcca catcttccgc ctgtgtaacg   1500
acctggcctc cgcatccgca gaaattgcac gcggcgaaac cgccaactcc gtatcctgct   1560
atatgcgtac caaaggcatc agcgaagaac tggctaccga atccgtgatg aacctgatcg   1620
atgaaacttg gaagaagatg aacaaagaaa aactgggcgg ttctctgttc gccaaaccat   1680
tcgttgaaac cgcgattaac ctggcgcgcc aatctcactg cacctatcat aacggtgacg   1740
cacacacctc cccggatgaa ctgacccgta agcgtgtgct gtccgttatt accgaaccaa   1800
ttctgccgtt cgaacgctaa tctagaggca tcaaataaaa cgaaaggctc agtcgaaaga   1860
ctgggccttt cgttttatct gttgtttgtc ggtgaacgct ctcctgagta ggacaaatcc   1920
gccgccctag acctagggga tatattccgc ttcctcgctc actgactcgc tacgctcggt   1980
cgttcgactg cggcgagcgg aaatggctta cgaacgggc ggagatttcc tggaagatgc    2040
caggaagata cttaacaggg aagtgagagg gccgcggcaa agccgttttt ccataggctc   2100
cgcccccctg acaagcatca cgaaatctga cgctcaaatc agtggtggcg aaacccgaca   2160
ggactataaa gataccaggc gtttccccct ggcggctccc tcgtgcgctc tcctgttcct   2220
gcctttcggt ttaccggtgt cattccgctg ttatggccgc gtttgtctca ttccacgcct   2280
gacactcagt tccgggtagg cagttcgctc caagctggac tgtatgcacg aacccccgt    2340 tcagtccgac cgctgcgcct tatccggtaa ctatcgtctt gagtccaacc cggaaagaca   2400
tgcaaaagca ccactggcag cagccactgg taattgattt agaggagtta gtcttgaagt   2460
catgcgccgg ttaaggctaa actgaaagga caagttttgg tgactgcgct cctccaagcc   2520
agttacctcg gttcaaagag ttggtagctc agagaacctt cgaaaaaccg ccctgcaagg   2580
cggttttttc gttttcagag caagagatta cgcgcagacc aaaacgatct caagaagatc   2640
```

```
atcttattaa tcagataaaa tattactaga tttcagtgca atttatctct tcaaatgtag    2700
cacctgaagt cagccccata cgatataagt tgttactagt gcttggattc tcaccaataa    2760
aaaacgcccg gcggcaaccg agcgttctga acaaatccag atggagttct gaggtcatta    2820
ctggatctat caacaggagt ccaagcgagc tctcgaaccc cagagtcccg ctcagaagaa    2880
ctcgtcaaga aggcgataga aggcgatgcg ctgcgaatcg ggagcggcga taccgtaaag    2940
cacgaggaag cggtcagccc attcgccgcc aagctcttca gcaatatcac gggtagccaa    3000
cgctatgtcc tgatagcggt ccgccacacc cagccggcca cagtcgatga atccagaaaa    3060
gcggccattt tccaccatga tattcggcaa caggcatcg ccatgggtca cgacgagatc    3120
ctcgccgtcg ggcatgcgcg ccttgagcct ggcgaacagt tcggctggcg cgagcccctg    3180
atgctcttcg tccagatcat cctgatcgac aagaccggct tccatccgag tacgtgctcg    3240
ctcgatgcga tgtttcgctt ggtggtcgaa tgggcaggta gccggatcaa gcgtatgcag    3300
ccgccgcatt gcatcagcca tgatggatac tttctcggca ggagcaaggt gagatgacag    3360
gagatcctgc cccggcactt cgcccaatag cagccagtcc cttcccgctt cagtgacaac    3420
gtcgagcaca gctgcgcaag gaacgcccgt cgtggccagc cacgatagcc gcgctgcctc    3480
gtcctgcagt tcattcaggg caccggacag gtcggtcttg acaaaaagaa ccgggcgccc    3540
ctgcgctgac agccggaaca cggcggcatc agagcagccg attgtctgtt gtgcccagtc    3600
atagccgaat agcctctcca cccaagcggc cggagaacct gcgtgcaatc catcttgttc    3660
aatcatgcga aacgatcctc atcctgtctc ttgatcagat cttgatcccc tgcgccatca    3720
gatccttggc ggcaagaaag ccatccagtt tactttgcag gcttcccaa ccttaccaga    3780 gggcgcccca gctggcaatt ccgacgtctg tgtggaattg tgagcggata caatttcac    3840 acagggccct cggacaccga ggagaatgtc aagaggcgaa cacacaacgt cttggagcgc    3900
cagaggagga acgagctaaa acggagcttt tttgccctgc gtgaccagat cccggagttg    3960
gaaaacaatg aaaaggcccc caaggtagtt atccttaaaa aagccacagc atacatcctg    4020
tccgtccaag cagaggagca aaagctcatt tctgaagagg acttgttgcg gaaacgacga    4080
gaacagttga aacacaaact tgaacagcta cggaactctt gtgcgtaagg aaaagtaagg    4140
aaaacgattc cttctaacag aaatgtcctg agcaatcacc tatgaactgt cgac          4194
```

<210> SEQ ID NO 15
<211> LENGTH: 4194
<212> TYPE: DNA
<213> ORGANISM: Artificial
<220> FEATURE:
<223> OTHER INFORMATION: pPROLAR-IspSm2

<400> SEQUENCE: 15

```
tcgagcatag cattttttatc cataagatta gcggatctaa cctttacaat tgtgagcgct    60
cacaattatg atagattcaa ttgtgagcgg ataacaattt cacacagaat tcattaaaga    120
ggagaaaggt accccatatg gcttgctctg tatccactga gaacgtatct ttcactgaga    180
ctgaaactga gacccgtcgc tctgcgaact atgagccaaa ctcttgggat tacgattatc    240
ggctgtcctc tgacactgac gaaagcattg aagtttacaa ggacaaagcg aaaaagctgg    300
aagcggaggt tcgtcgcgaa atcaacaacg agaaagctga attcctgact ctgctggagc    360
tgatcgacaa cgtacagcgt ctgggtctgg gttaccgttt cgagtctgac atccgccgtg    420
ctctggatcg cttcgtttcc agcggcggtt tcgatgcagt gaccaagact agcctgcatg    480
cgaccgcgct gtctttccgt ctgctgcgtc agcacggttt tgaagtttct caggaagcgt    540
```

-continued

```
tctctggctt caaggaccag aacggtaatt tcctggaaaa cctgaaggag gacattaagg    600
cgattctgtc cctgtacgaa gcgtcttttc tggcgctgga aggcgagaac atcctggacg    660
aagcgaaagt attcgcaatc tcccacctga agaactgagc gaagaaaaa atcggtaaag    720 atctggcgga acaggtgaac cacgctctgg aactgcctct gcatcgtcgt acccagcgtc    780
tggaggctgt gctgtccatt gaagcatacc gtaagaaaga agatgcagat caggttctgc    840
tggaactggc gatcctggac tacaacatga ttcagtctgt gtaccagcgt gacctgcgtg    900
aaacctctcg ctggtggcgc cgtgtgggtc tggcaaccaa actgcacttc gcacgcgatc    960
gtctgattga atccttctac tgggctgtag gcgtggcctt cgaaccgcag tactccgatt   1020
gccgtaactc tgttgctaaa atgttctctt tcgttaccat tatcgatgac atctatgacg   1080
tttatggtac cctggatgaa ctggagctgt tcaccaacgc agttgaacgc tgggacgtta   1140
acgcgattga tgacctgcct gactacatga aactgtgctt cctggcgctg tataacacta   1200
tcaacgagat cgcgtatgat aacctgaaag aaaaaggtga aaacattctg ccgtatctga   1260
ccaaagcctg ggccgacctg tgtaacgcat tcctgcagga ggccaaatgg ctgtacaata   1320
agtctactcc tactttcgac gattacttcg gtaacgcttg gaaatctagc ctggcccgc    1380 tgcaactggt cttcgcctat ttcgcggtag tgcaaaacat caaaaaggaa gagatcgaga   1440
atctgcagaa atatcacgac attatctccc gcccgagcca catcttccgc ctgtgtaacg   1500
acctggcctc cgcatccgca gaaattgcac gcggcgaaac cgccaactcc gtatcctgct   1560
atatgcgtac caaaggcatc agcgaagaac tggctaccga atccgtgatg aacctgatcg   1620
atgaaacttg gaagaagatg aacaaagaaa aactgggcgg ttctctgttc gccaaaccat   1680
tcgttgaaac cgcgattaac ctggcgcgcc aatctcactg cacctatcat aacggtgacg   1740
cacacacctc cccggatgaa ctgacccgta agcgtgtgct gtccgttatt accgaaccaa   1800
ttctgccgtt cgaacgctaa tctagaggca tcaaataaaa cgaaaggctc agtcgaaaga   1860
ctgggccttt cgttttatct gttgtttgtc ggtgaacgct ctcctgagta ggacaaatcc   1920
gccgccctag acctagggga tatattccgc ttcctcgctc actgactcgc tacgctcggt   1980
cgttcgactg cggcgagcgg aaatggctta cgaacggggc ggagatttcc tggaagatgc   2040
caggaagata cttaacaggg aagtgagagg gccgcggcaa agccgttttt ccataggctc   2100
cgcccccctg acaagcatca cgaaatctga cgctcaaatc agtggtggcg aaacccgaca   2160
ggactataaa gataccaggc gtttcccct ggcggctccc tcgtgcgctc tcctgttcct   2220
gcctttcggt ttaccggtgt cattccgctg ttatggccgc gtttgtctca ttccacgcct   2280
gacactcagt tccgggtagg cagttcgctc caagctggac tgtatgcacg aaccccccgt   2340
tcagtccgac cgctgcgcct tatccggtaa ctatcgtctt gagtccaacc cggaaagaca   2400
tgcaaaagca ccactggcag cagccactgg taattgattt agaggagtta gtcttgaagt   2460
catgcgccgg ttaaggctaa actgaaagga caagttttgg tgactgcgct cctccaagcc   2520
agttacctcg gttcaaagag ttggtagctc agagaaccct cgaaaaaccg ccctgcaagg   2580
cggttttttc gttttcagag caagagatta cgcgcagacc aaaacgatct caagaagatc   2640
atcttattaa tcagataaaa tattactaga tttcagtgca atttatctct tcaaatgtag   2700
cacctgaagt cagccccata cgatataagt tgttactagt gcttggattc tcaccaataa   2760
aaaacgcccg gcggcaaccg agcgttctga acaaatccag atggagttct gaggtcatta   2820
ctggatctat caacaggagt ccaagcgagc tctcgaaccc cagagtcccg ctcagaagaa   2880
```

|  |  |
|---|---|
| ctcgtcaaga aggcgataga aggcgatgcg ctgcgaatcg ggagcggcga taccgtaaag | 2940 |
| cacgaggaag cggtcagccc attcgccgcc aagctcttca gcaatatcac gggtagccaa | 3000 |
| cgctatgtcc tgatagcggt ccgccacacc cagccggcca cagtcgatga atccagaaaa | 3060 |
| gcggccattt ccaccatga tattcggcaa gcaggcatcg ccatgggtca cgacgagatc | 3120 |
| ctcgccgtcg ggcatgcgcg ccttgagcct ggcgaacagt tcggctggcg cgagcccctg | 3180 |
| atgctcttcg tccagatcat cctgatcgac aagaccggct tccatccgag tacgtgctcg | 3240 |
| ctcgatgcga tgtttcgctt ggtggtcgaa tgggcaggta gccggatcaa gcgtatgcag | 3300 |
| ccgccgcatt gcatcagcca tgatggatac tttctcggca ggagcaaggt gagatgacag | 3360 |
| gagatcctgc cccggcactt cgcccaatag cagccagtcc cttcccgctt cagtgacaac | 3420 |
| gtcgagcaca gctgcgcaag gaacgcccgt cgtggccagc cacgatagcc gcgctgcctc | 3480 |
| gtcctgcagt tcattcaggg caccggacag gtcggtcttg acaaaaagaa ccgggcgccc | 3540 |
| ctgcgctgac agccggaaca cggcggcatc agagcagccg attgtctgtt gtgcccagtc | 3600 |
| atagccgaat agcctctcca cccaagcggc cggagaacct gcgtgcaatc catcttgttc | 3660 |
| aatcatgcga aacgatcctc atcctgtctc ttgatcagat cttgatcccc tgcgccatca | 3720 |
| gatccttggc ggcaagaaag ccatccagtt tactttgcag gcttccaa ccttaccaga | 3780 |
| gggcgcccca gctggcaatt ccgacgtctg tgtggaattg tgagcggata caatttcac | 3840 |
| acagggccct cggacaccga ggagaatgtc aagaggcgaa cacacaacgt cttggagcgc | 3900 |
| cagaggagga acgagctaaa cggagctttt tttgccctgc gtgaccagat cccggagttg | 3960 |
| gaaaacaatg aaaaggcccc caaggtagtt atccttaaaa aagccacagc atacatcctg | 4020 |
| tccgtccaag cagaggagca aaagctcatt tctgaagagg acttgttgcg gaaacgacga | 4080 |
| gaacagttga acacaaaact tgaacagcta cggaactctt gtgcgtaagg aaaagtaagg | 4140 |
| aaaacgattc cttctaacag aaatgtcctg agcaatcacc tatgaactgt cgac | 4194 |

<210> SEQ ID NO 16
<211> LENGTH: 74
<212> TYPE: DNA
<213> ORGANISM: Artificial
<220> FEATURE:
<223> OTHER INFORMATION: TRC promoter

<400> SEQUENCE: 16

|  |  |
|---|---|
| ttgacaatta atcatccggt ccgtataatc tgtggaattg tgagcggata acaatttcac | 60 |
| acaggaaaca gacc | 74 |

<210> SEQ ID NO 17
<211> LENGTH: 1426
<212> TYPE: DNA
<213> ORGANISM: Artificial
<220> FEATURE:
<223> OTHER INFORMATION: ACE promoter

<400> SEQUENCE: 17

|  |  |
|---|---|
| gcttatcgat tgctggtcga acgtccggc tttctcaaaa ggtttaccaa tggcttccat | 60 |
| cgcgcgagcc gcatacggac gggaaagggt taactccggt ttgcctttgg cgaactctgg | 120 |
| agaggcggtg ttatggcaat cggcacaacc taagttgttg acgatttccg gaccgccgcg | 180 |
| cgcccattta ccgtggaagt agccatcttc gccgtctttc tggatcagac gcgccacatc | 240 |
| cgggctttta caactccagc atgccatcgg tagcggacca tcttcagcgt ttttcggcgc | 300 |
| accggtacgc agggtttcac gcacatcggt cacagcaaaa gcatgtccac gcggcttgtt | 360 |

```
gtaatcgcgc gagaagggat accccgccca caggatcacc agccgtggat cttccgccag      420
ggcgtcaaca cgctctgact gttccgaggt ggctttccag gagagatatt gatcgggatg      480
ctgcggggca aaggtttcat tcttcgcttc cacagttaca ggttttgcgg gagcagccgt      540
ttgttcagcg tgaacagaag tgaaaaagaa aaaggaatc aataagctga agatacggcg       600
tgcgtttatt tttatccttg tcatagggc ttcatccgaa ttgcgccatt gttgcaatgg       660
cggtttttat tgtttttcac gacagtaacc gcacctacac tgtcatgaca ttgctcgccc      720
ctatgtgtaa caaataacca cactgtgaat gttgtcttta atcaattgta agtgcatgta      780
aaataccact ttagagttag tcagtatctt cctcttttc aacagcatgc ataactgcat       840
gttcctcaaa gaattaatca acttttgttg ctgaccttca aaaattaccc tgccgtttat      900
ttgcacaatt ctacttttgc gtgatttgtt cgcccaaatt tttaaccaaa atgcccaata     960
cccgtacatt taacggttat gccacatatt attaacatcc tacaaggaga acaaaagcat      1020
gagccaaatt cacaaacaca ccattcctgc caacatcgca gaccgttgcc tgataaacct     1080
tcagcagtac gaggcgatgt atcaacaatc tattaacgta cctgatacct tctggggcga     1140
acagggaaaa attcttgact ggatcaaacc ttaccagaag gtgaaaaaca cctcctttgc     1200
ccccggtaat gtgtccatta aatggtacga ggacgacacg ctgaatctgg cggcaaactg    1260
ccttgaccgc catctgcaag aaaacggcga tcgtaccgcc atcatctggg aaggcgacga    1320
cgccagccag agcaaacata tcagctataa agagctgcac cgcgacgtct gccgcttcgc    1380
caataccctg ctcgagaata agaaggagaa ttaagaagga gatata                    1426
```